United States Patent
Kitagawa

(10) Patent No.: US 6,218,440 B1
(45) Date of Patent: Apr. 17, 2001

(54) HYDROPHILIC POLYMERIC MATERIAL AND METHOD OF PREPARATION

(75) Inventor: Naotaka Kitagawa, Fremont, CA (US)

(73) Assignee: Biopore Corporation, Los Gatos, CA (US)

(*) Notice: Subject to any disclaimer, the term of this patent is extended or adjusted under 35 U.S.C. 154(b) by 0 days.

(21) Appl. No.: 09/624,711

(22) Filed: Jul. 25, 2000

Related U.S. Application Data

(60) Continuation of application No. 09/427,965, filed on Oct. 27, 1999, which is a division of application No. 08/883,950, filed on Jun. 27, 1997, now Pat. No. 6,048,908.

(51) Int. Cl.$^7$ ....................................................... C08J 9/28
(52) U.S. Cl. .............................. 521/56; 521/64; 521/65; 521/71; 521/72
(58) Field of Search ................................ 521/56, 64, 65, 521/71, 72

(56) References Cited

U.S. PATENT DOCUMENTS

| | | |
|---|---|---|
| 3,255,127 | 6/1966 | von Bonin . |
| 3,460,972 | 8/1969 | Nuck ........................................ 117/72 |
| 3,737,337 | 6/1973 | Schnoring et al. ................... 117/100 |
| 3,822,224 | 7/1974 | Gillan et al. . |
| 3,879,314 | 4/1975 | Gunning et al. . |
| 3,891,577 | 6/1975 | Kershaw et al. . |
| 3,923,704 | 12/1975 | Gunning et al. . |
| 3,933,579 | 1/1976 | Kershaw et al. . |
| 3,943,063 | 3/1976 | Morishita et al. ................... 252/316 |
| 3,988,508 | 10/1976 | Lissant . |
| 4,137,380 | 1/1979 | Gunning et al. . |
| 4,321,332 | 3/1982 | Beresford et al. . |
| 4,384,975 | 5/1983 | Fong .............................. 427/213.36 |
| 4,401,456 | 8/1983 | Connick, Jr. ............................. 71/88 |
| 4,522,953 | 6/1985 | Barby et al. . |
| 4,536,521 | 8/1985 | Haq . |
| 4,690,825 | 9/1987 | Won .................................... 424/501 |
| 4,741,872 | 5/1988 | De Luca et al. ..................... 264/4.7 |
| 4,818,542 | 4/1989 | DeLuca et al. ...................... 424/491 |
| 4,873,091 | 10/1989 | Jankower et al. ................... 424/489 |
| 4,888,309 | 12/1989 | Araya . |
| 4,898,734 | 2/1990 | Mathiowitz et al. ................ 424/426 |
| 5,064,570 | 11/1991 | Rohringer . |
| 5,071,747 | 12/1991 | Hough et al. . |
| 5,073,365 | 12/1991 | Katz et al. .......................... 424/489 |
| 5,135,740 | 8/1992 | Katz et al. .......................... 424/401 |
| 5,135,872 | 8/1992 | Pouletty et al. ..................... 436/180 |
| 5,145,675 | 9/1992 | Won et al. ........................ 424/78.31 |
| 5,154,713 | 10/1992 | Lind .................................... 521/149 |
| 5,169,904 | 12/1992 | Ziemelis et al. .................... 521/149 |
| 5,246,714 | 9/1993 | Dahlinder et al. .................. 424/497 |
| 5,292,777 | 3/1994 | DesMarais et al. . |
| 5,316,774 | 5/1994 | Eury et al. .......................... 424/501 |
| 5,352,711 | 10/1994 | DesMarais . |
| 5,354,548 | 10/1994 | Araya et al. . |
| 5,387,207 | 2/1995 | Dyer et al. . |
| 5,393,528 | 2/1995 | Staab .................................. 424/436 |
| 5,397,316 | 3/1995 | LaVon et al. . |
| 5,422,123 | 6/1995 | Conte et al. ........................ 424/479 |
| 5,425,265 | 6/1995 | Jaisinghani ............................ 73/38 |
| 5,458,890 | 10/1995 | Williford et al. ....................... 426/3 |
| 5,500,451 | 3/1996 | Goldman et al. . |
| 5,550,167 | 8/1996 | DesMarais . |
| 5,563,179 | 10/1996 | Stone et al. . |
| 5,583,162 | 12/1996 | Li et al. . |

(List continued on next page.)

FOREIGN PATENT DOCUMENTS

| | | |
|---|---|---|
| WO 95/31187 | 11/1995 | (WO) . |
| WO 95/31485 | 11/1995 | (WO) . |
| WO 96/21474 | 7/1996 | (WO) . |
| WO 96/21475 | 7/1996 | (WO) . |
| WO 96/21682 | 7/1996 | (WO) . |
| WO 96/22796 | 8/1996 | (WO) . |
| WO 96/40823 | 12/1996 | (WO) . |
| WO 97/32612 | 9/1997 | (WO) . |
| WO 98/00085 | 1/1998 | (WO) . |
| WO 95/31498 | 11/1998 | (WO) . |

OTHER PUBLICATIONS

Atyabi, F. et al., "Controlled Drug Release From Coated Floating Ion Exchange Resin Beads,"42 *Journal of Controlled Release* 25–28 (1996).

Brooke, D. and Washkuhn, R., "Zero–Order Drug Delivery System: Theory and Preliminary Testing," 66(2) *Journal of Pharmaceutical Sciences* 159–162 (Feb. 1977).

Crotts, G., and Park, T., "Preparation of Porous and Non-porous Biodegradable Polymeric Hollos Microspheres," 35 *Journal of Controlled Release* 91–105 (1995).

DeLuca, P. et al., "Biodegradable Polyesters for Drug and Polypeptide Delivery" 203rd National Meeting of the American Chemical Society 53–79 (Apr. 5–10, 1992) in *Polymeric Delivery Systems*, El–Nokaly, M. et al, eds.

Harland, R. et al. "A Model of Dissolution–Controlled, Diffusional Drug Release From Non–Swellable Polymeric Microspheres." 7 *Journal of Controlled Release* 207–215 (1988).

(List continued on next page.)

*Primary Examiner*—Morton Foelak
(74) *Attorney, Agent, or Firm*—McCutchen, Doyle, Brown, Enersen, LLP; David W. Maher

(57) ABSTRACT

The present invention relates to a porous crosslinked hydrophilic polymeric material having cavities joined by interconnecting pores wherein at least some of the cavities at the interior of the material communicate with the surface of the material. The present invention also relates to a process for producing the polymeric material. This process involves combining a hydrophilic monomer phase with an oil discontinuous phase to form an emulsion, and polymerizing the emulsion. The emulsion can be a high internal phase emulsion (i.e., a "HIPE"). The polymeric material can be produced in a variety of forms. In one embodiment the emulsion is suspended in an oil suspension medium, and emulsion droplets are polymerized to produce polymeric microbeads.

28 Claims, 3 Drawing Sheets

U.S. PATENT DOCUMENTS

| | | |
|---|---|---|
| 5,632,737 | 5/1997 | Stone et al. . |
| 5,633,291 | 5/1997 | Dyer et al. . |
| 5,650,222 | 7/1997 | DesMarais et al. . |
| 5,653,922 | 8/1997 | Li et al. . |
| 5,760,097 | 6/1998 | Li et al. ................................. 521/61 |
| 5,840,293 | 11/1998 | Nacht et al. ....................... 424/78.02 |
| 5,863,957 | 1/1999 | Li et al. ................................. 521/61 |
| 5,871,722 | 2/1999 | Nacht et al. ....................... 424/78.03 |

OTHER PUBLICATIONS

Hermann, J. and Bodmeier, R., "The Effect of Particle Microstructure on the Somatostatin Release From Poly (Lactide) Microspheres Prepared by a W/O/W Solvent Evaporation Method," 36 *Journal of Controlled Release* 63–71 (1995).

Hsieh, D. et al. "Zero–Order Controlled–Release Polymer Matrices for Micro– and Macromolecules," 72(1) *Journal of Pharmaceutical Sciences* 17–22 (Jan. 1983).

Jeyanthi, R. et al., "Effect of Solvent Removal Technique On the Matrix Characteristics of Polylactide/Glycolide Microspheres for Peptide Delivery," 38 *Journal of Controlled Release* 235–244 (1996).

Kissel, T. et al. "Parenteral Protein Delivery Systems Using Biodegradable Polyesters of ABA Block Structure, Containing Hydrophobic Poly (lactide–co–glycolide) A Blocks and Hydrophilic Poly (ethylene oxide) B Blocks," 39 *Journal of Controlled Release* 315–326 (1996).

Koyama, Y. et al., "Receptor–Mediated Absorption of High Molecular Weight Dextrans From Intestinal Tract," 41 *Journal of Controlled Release* 171–176 (1996).

Kyo, M. et al., "Effects of Preparation Conditions of Cisplatin–Loaded Microspheres on the In Vitro Release," 35 *Journal of Controlled Release* 73–82 (1995).

Langer, R., "Polymer Systems For Controlled Release of Macromolecules, Immobilized Enzyme Medical Bioreactors, and Tissue Engineering," 19 *Advances in Chemical Engineering* 1–50 (1994).

Mathlowitz, E. et al., "Biologically Erodable Microspheres As Potential Oral Drug Delivery Systems," 386 *Nature* 410–414 (Mar. 1997).

McGee, J. et al. "Zero Order Release of Protein From Poly (D,L–lactide–co–glycolide) Microparticles Prepared Using a Modified Phase Separation Technique, " 34 *Journal of Controlled Release* 77–86 (1995).

Santus, G. and Baker, R. "Osmotic Drug Delivery: A Review of the Patent Literature," 35 *Journal of Controlled Release* 1–21 (1995).

Youxin, L. and Kissel, T. "Synthesis and Properties of Biodegradable ABA Triblock Copolymers Consisting of Poly (L–lactic acid) or Poly (L–lact–co–glycolic acid) A–Blocks Attached to Central Poly (Oxyethylene) B–Blocks," 27 *Journal of Controlled Release* 247–257 (1993).

HYDROPHILIC POLYMERIC MATERIAL AND METHOD OF PREPARATION

CROSS-REFERENCE TO RELATED APPLICATIONS

This is a continuation of application Ser. No. 09/427,965, filed Oct. 27, 1999, which is a division of application Ser. No. 08/883,950, filed Jun. 27, 1997, now U.S. Pat. No. 6,048,908, issued Apr. 11, 2000.

STATEMENT REGARDING FEDERALLY SPONSORED RESEARCH OF DEVELOPMENT

Not applicable

BACKGROUND OF THE INVENTION

1. Field of the Invention

The present invention relates hydrophilic crosslinked porous polymeric materials and methods for preparing such materials. In one embodiment, the hydrophilic polymeric materials are produced in the form of microbeads.

2. Description of the Related Art

Crosslinked porous polymeric materials are disclosed. in U.S. Pat. No. 4,522,953 (Barby et al., issued Jun. 11, 1985). The disclosed polymeric materials are produced by polymerization of "water-in-oil" emulsions having a relatively high ratio of water to oil, typically on the order of 70% or more. These emulsions are termed "high internal phase emulsions" and are known in the art as "HIPEs." The HIPEs disclosed in U.S. Pat. No. 4,522,953 comprise an oil continuous phase including a monomer and a crosslinker and an aqueous discontinuous phase. Such emulsions are prepared by subjecting the combined oil and water phases to agitation in the presence of an emulsifier. Polymers are produced from the resultant emulsion by heating or other means. The polymers are then washed to remove any unpolymerized emulsion components.

The disclosed porous polymers have rigid structures characterized by cavities interconnected by pores in the cavity walls. By choosing appropriate component and process conditions, HIPE polymers with void volumes of 70% or more can be achieved. These materials thus have a very high capacity for absorbing and retaining liquids.

Although the polymerization of oil-phase monomer and crosslinker described by Barby and others produced hydrophobic HIPE polymers, such polymers could be made hydrophilic by conjugation with hydrophilic groups. For instance, U.S. Pat. No. 4,536,521 (Haq, issued Aug. 20, 1985) discloses that HIPE polymers can be sulfonated to produce a sulfonated polymeric material that exhibits a high capacity for absorption of ionic solutions. Other functionalized HIPE polymers prepared by a similar process have been disclosed in U.S. Pat. No. 4,611,014 (Jomes et al., issued Sep. 9, 1986) and U.S. Pat. No. 4,612,334 (Jones et al., Sep. 16, 1986).

Initially processes for making HIPE polymers produced blocks of polymeric material the size and shape of the vessel used for polymerization. A problem with producing HIPE polymers in block form was that it is very difficult to wash unpolymerized emulsion components out of blocks of low density, highly absorbent material. Attempts to address this problem by grinding the blocks into particles were unsatisfactory because both the drying and milling processes are costly, and there is a limit to the size of the particles produced by milling.

The state of the art was significantly advanced by producing HIPE polymers in the form of microbeads, as disclosed in U.S. Pat. No. 5,583,162 (Li et al., issued Dec. 10, 1996) and International Application No. PCT/US95/06879 (WO 95/33553, published Dec. 14, 1995). The disclosed "HIPE microbeads" are produced by polymerization of a suspension of HIPE droplets. A key feature of one polymerization method described in International Application No. PCT/US95/06879 was the use of a film-forming stabilizer to reduce leakage of the discontinuous phase of the HIPE from HIPE droplets into the medium in which the droplets were dispersed. This aspect of the method helped preserve the HIPE-like structure of the droplets upon conversion to microbeads.

It is desirable to produce hydrophilic polymeric materials having a HIPE-like structure directly, i.e., by polymerizing hydrophilic monomers. The polymerization of hydrophilic monomers in an "oil-in-water-in-oil" emulsion is described in U.S. Pat. No. 4,742,086 (Masamizu, issued May 3, 1988). According to this process, an oil-in-water emulsion is prepared and added to a hydrophobic dispersing medium. The process is disclosed as useful for preparing polymeric beads from oil-in-water emulsions that are less than 70% oil (internal) phase. Thus, the resultant hydrophilic beads are not HIPE microbeads.

BRIEF SUMMARY OF THE INVENTION

The present invention includes a process based upon polymerization of hydrophilic monomers, which produces porous crosslinked hydrophilic polymeric materials directly. This process provides the significant advantage of allowing the preparation of hydrophilic polymers from HIPEs (i.e., emulsions containing about 70% to about 99% internal phase).

This process is carried out by forming and then polymerizing an emulsion including a hydrophilic monomer continuous phase and an oil discontinuous phase. The emulsion includes a hydrophilic monofunctional monomer, a polyfunctional crosslinker, an emulsifier having a hydrophobic cyclic head group and a hydrophilic tail, and an organic solvent. The use of an emulsifier having a hydrophobic cyclic head group and a hydrophilic tail has been found to be particularly effective in maintaining the stability of the emulsion during polymerization, especially when the emulsion is a HIPE.

This process can be used to produce hydrophilic polymers in a variety of forms, including microbeads. To produce hydrophilic microbeads, a stabilizer that is a film-forming compound is included in the emulsion, and the emulsion is added to an oil suspension medium to form a suspension of emulsion droplets. Polymerization then converts the emulsion droplets to microbeads. In one embodiment, the stabilizer is a natural or synthetic polymeric stabilizer.

The invention also includes porous crosslinked hydrophilic polymeric microbeads, in particular, hydrophilic microbeads produced by the process of the invention.

Also included are porous crosslinked hydrophilic polymeric microbeads having cavities joined by interconnecting pores, wherein at least some of the cavities at the interior of the microbeads communicate with the surface of the microbeads. At least approximately 10% of the microbeads are substantially spherical or substantially ellipsoidal or a combination thereof. The microbeads have a nominal void volume of at least about 70% and a water absorption capacity of at least about 5 grams of water per gram of dry polymer. Because of this high absorption capacity, these microbeads are useful in a variety of applications, including absorption of bodily fluids, absorption or transport of solvents or other chemicals, and scavenging of, e.g., aqueous fluids.

In one embodiment, the hydrophilic microbeads reach half maximal absorption capacity within 1 minute after immersion. These microbeads are particularly useful in applications requiring rapid absorption rates.

DETAILED DESCRIPTION OF THE INVENTION

The present invention includes a crosslinked porous hydrophilic polymeric material (hereafter a "hydrophilic polymer"). A preferred hydrophilic polymer is produced from monomers and crosslinkers wherein at least 50% by weight of the total polymerizable monomer (i.e., monomer plus crosslinker) is hydrophilic. More preferably, at least 70%, and even more preferably at least 90% by weight of the total polymerizable monomer is hydrophilic. If desired, 100% by weight of the total polymerizable monomer can be hydrophilic.

Figure 1A:
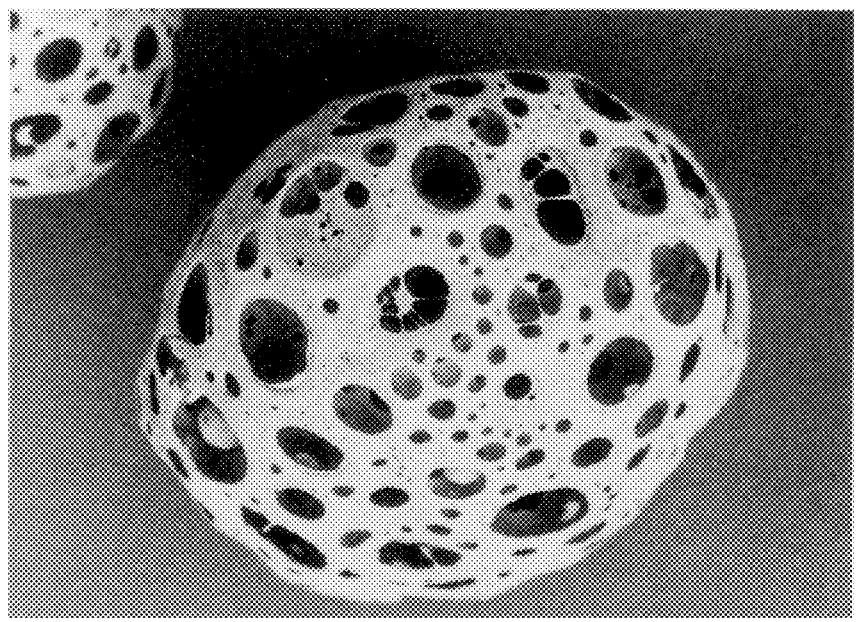
FIG. 1A shows a scanning electron micrograph of a dry hydrophilic microbead produced as described in Example 3, Table 11. All micrographs herein were taken using Hitachi Scanning Electron Microscope Model No. S-3200. The magnification is 120×.
Figure 1B:
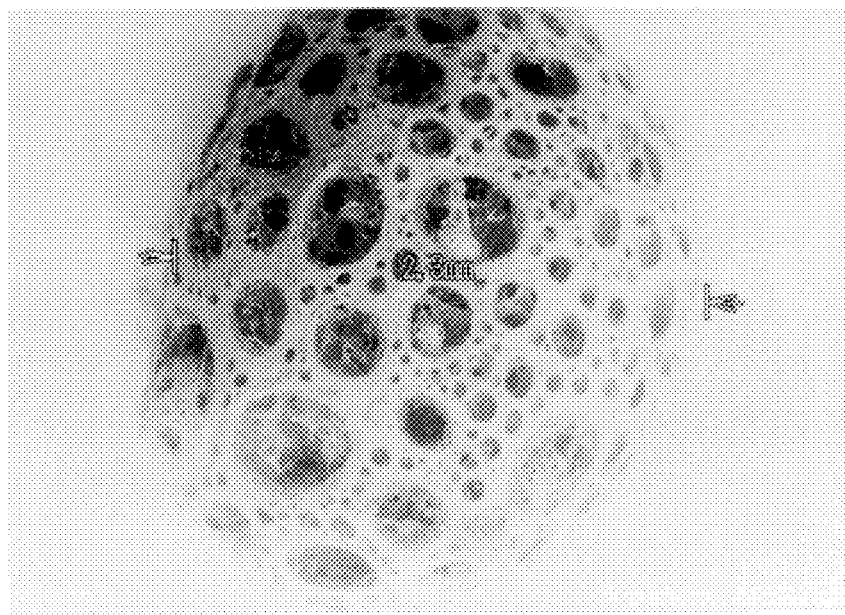
FIG. 1B shows a scanning electron micrograph of the hydrbphilic microbead of FIG. 1A in which the hydrophilic microbead is saturated with water. The magnification is 30×.
Figure 2:
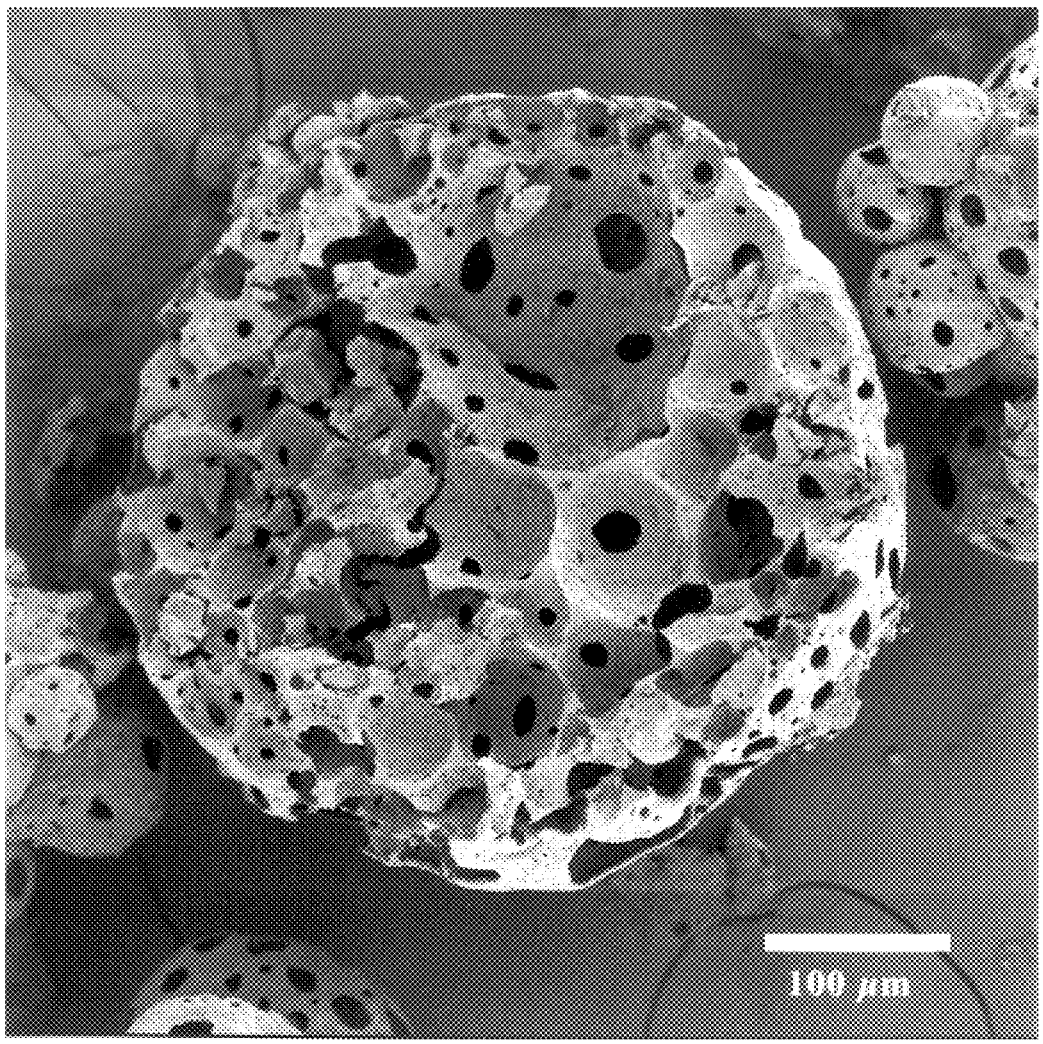
FIG. 2 shows a scanning electron micrograph of the internal structure of a dry hydrophilic microbead produced as described in Example 1. The magnification is 150×.
Figure 3A:
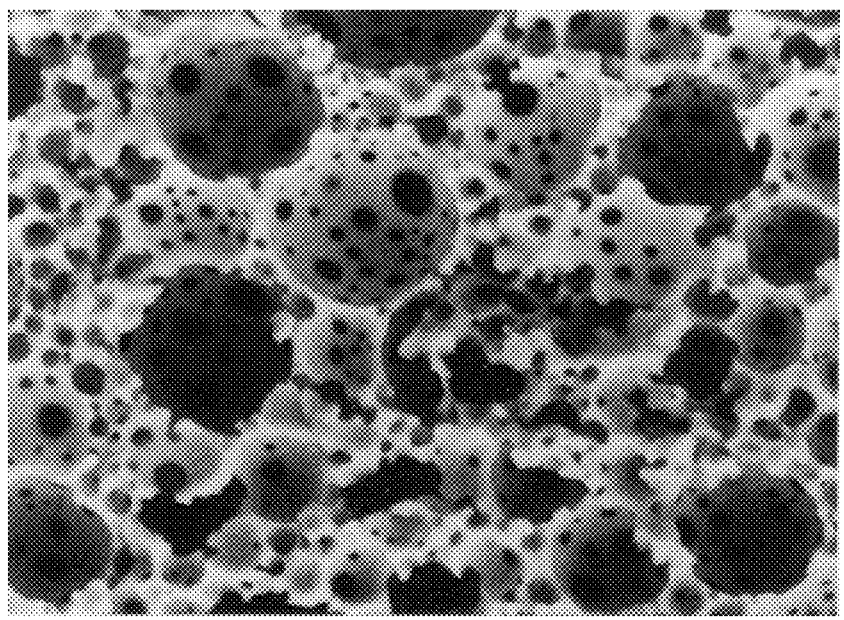
FIG. 3A shows a scanning electron micrograph of a cross-section through a dry hydrophilic block produced as described in Example 4. The magnification is 1500×.
Figure 3B:
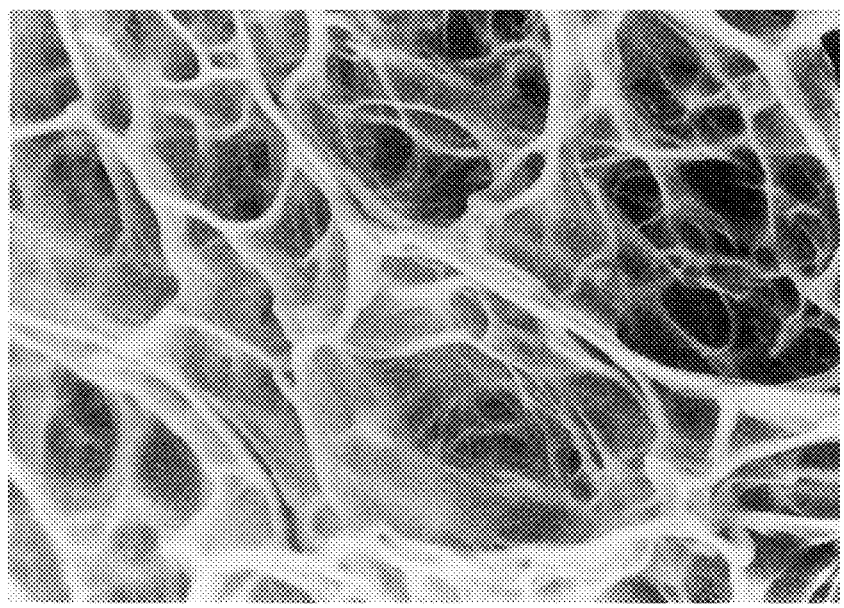
FIG. 3B shows a scanning electron micrograph of the internal structure of the hydrophilic microbead of FIG. 3B in which the hydrophilic microbead is saturated with water. The magnification is 1500×.

In one embodiment, a hydrophilic polymer that is at least about 2% crosslinked has a HIPE-like structure. See FIGS. 1–3. This structure is characterized by cavities joined by interconnecting pores. See, e.g, FIGS. 1A and B.

The hydrophilic polymer is produced by polymerizing an emulsion. The emulsion can be polymerized by any suitable method, and the selection of a polymerization method depends, in part, on the desired shape of the hydrophilic polymer. For example, bulk polymerization (i.e., direct polymerization of the emulsion) can be initiated after forming or pouring the emulsion into a container, in which case, the resultant material generally takes the form of the container.

Bulk polymerization can also be carried out by extruding the emulsion from a nozzle into a hot gas. The temperature increase induces polymerization in the emulsion as it falls. The emulsion is extruded as a stream to produce a cylindrical material or in the form of droplets to produce beads.

Bulk polymerization is exemplified herein by the production of a block of polymeric material. Therefore, for ease of discussion, any hydrophilic polymer produced by bulk polymerization is referred to herein as a "hydrophilic block," which term does not imply any limitation with regard to shape.

Alternatively, polymerization of the emulsion can be initiated after forming a suspension of emulsion droplets. In this case, polymerization produces microbeads (termed "hydrophilic microbeads"). At least about 10% of the hydrophilic microbeads produced in this manner are substantially spherical and or substantially ellipsoidal. Preferably, at least about 20% and more preferably at least about 50% of this material consists of substantially spherical and/or substantially ellipsoidal hydrophilic microbeads.

The present invention also includes processes for making hydrophilic polymers in which an emulsion including an "oil discontinuous phase" in a "hydrophilic monomer phase" is polymerized. Hydrophilic microbeads, for example, are typically produced by suspension polymerization of such an emulsion. In one embodiment, the emulsion is a high internal phase emulsion, termed a "HIPE," wherein the emulsion contains at least about 70%, by weight, oil discontinuous phase. The hydrophilic polymers produced from such an emulsion are termed "hydrophilic HIPE blocks" (i.e., hydrophilic HIPE polymers produced by bulk polymerization) or hydrophilic HIPE microbeads" (i.e., hydrophilic HIPE polymers typically produced by emulsion polymerization). In other embodiments, hydrophilic blocks or microbeads can be produced from an emulsion containing a lower percentage of oil discontinuous phase.

Definitions

As used herein to describe the polymers of the invention, the term "hydrophilic" refers to polymers produced from one or more hydrophilic monomers and/or crosslinkers. A hydrophilic monomer or crosslinker is defined herein as any monomer or crosslinker wherein at least about 50% of the monomer or crosslinker dissolved in a 50:50 oil:water mixture partitions into the water phase when the mixture is allowed to separate into two phases.

As used herein to describe hydrophilic microbeads, the terms "substantially spherical" or "substantially ellipsoidal" indicate microbeads having a smooth, rounded shape, such as, for example, those produced by polymerization of dispersed droplets.

As applied to hydrophilic polymers, the phrase "in the dry state" refers to hydrophilic polymers dried by any conventional method, such as for example, air-drying for two days or drying under vacuum at about 50–60° C. overnight.

As used herein with regard to hydrophilic microbeads, the term "average diameter" is the value obtained using a particle size analyzer, such as for example, the SediGraph 5100, which is commercially available from Micromeritics (Norcross, Ga.). Alternatively, average diameter can be determined by measuring the diameters of at least 100 microbeads in a photograph(s) taken using an optical microscope.

As used herein with regard to hydrophilic polymers, the term "bulk density" refers to the mass of a polymer divided by the total volume occupied by the polymer (which includes the volume of the solid portions of the polymer, the total void volume of the polymer, and, for a polymer in microbead form, the volume of the spaces between individual microbeads). For microbeads, this value is derived by pouring a batch of microbeads into a vessel that allows a determination of total microbead volume (e.g., a graduate cylinder), obtaining the mass (in grams) of the microbeads, and dividing the mass by the total volume (in milliliters). Bulk densities are given herein for hydrophilic microbeads in the dry state.

As used herein, the term "void volume" refers to the average volume of a polymer that does not include polymeric material. The term "nominal void volume" is defined as the volume percentage of the oil discontinuous phase in the emulsion used to produce the polymer. Accordingly, a hydrophilic polymer produced from an emulsion containing 80% oil discontinuous phase is said to have a nominal void volume of 80%, although those skilled in the art understand that the actual void volume of a given hydrophilic polymer may be different from the nominal void volume. In particular, dry hydrophilic polymers tend to have void volumes that are lower than their nominal void volumes, and wetting of such polymers can cause swelling, such that void volumes are higher than the nominal void volumes.

As used herein, the term "degree of crosslinking" refers to the amount of crosslinker in a crosslinked polymer expressed as a weight percentage of total polymerizable monomer (i.e., monomer plus crosslinker).

The term "oil" is used herein with regard to the discontinuous phase of the emulsion and the suspension medium described herein to indicate that these media are hydrophobic and therefore immiscible with the hydrophilic monomer phase (i.e., when either of these media are mixed with the hydrophilic monomer phase, and the mixture is allowed to stand at ambient temperature, the mixture separates into two phases). This term does not imply that these two phases must consist of or include oils.

Hydrophilic Polymers

The nominal void volume of a hydrophilic polymer according to the invention can be about 10%, about 20%, about 30%, about 40%, about 50%, or about 60%, and as high as about 99%. Upon drying, hydrophilic polymers shrink somewhat, which typically reduces the nominal void volume.

The bulk density of hydrophilic polymers can be very low and typically ranges from about 0.001 gm/mL to about 1.0 gm/mL. Preferably, the bulk density is between about 0.01 gm/mL and about 0.8 gm/mL.

The degree of crosslinking of the hydrophilic polymers described herein is generally at least about 0.01%. However, the shrinkage and/or deformation of polymer structure that can occur upon drying can be reduced by increasing the degree of crosslinking. For example, to maintain hydrophilic polymer porosity, the degree of crosslinking is generally at least about 2% and preferably at least about 5%. Crosslinking usually does not exceed 50%. Deformation can also be reduced by producing "chemically stiffened" hydrophilic polymers, as described in detail below.

Extremely absorbent hydrophilic polymers can be produced that exhibit a water or saline (i.e., 0.9% weight/volume solution) absorption capacity of at least about 5 grams of fluid per gram of dry polymer, when absorption is measured as described in Example 6. Preferably, absorbent hydrophilic polymers have a water or saline absorption capacity of at least about 10 grams of fluid per gram of dry polymer and more preferably at least about 100 grams of fluid per gram of dry polymer. In one embodiment, the water or saline absorption capacity of absorbent hydrophilic polymers is at least 300 grams of fluid per gram of dry polymer. The water or saline absorption capacity of hydrophilic polymers does not usually exceed 1000 grams of fluid per gram of dry polymer.

In addition, to absorbing large amounts of water, hydrophilic polymers described herein exhibit rapid rates of absorption. For example, hydrophilic polymers can be produced that absorb a volume of fluid that is approximately equal to 50% of their maximal absorption capacity within about 1 minute of immersion. Such polymers are said to "reach half maximal absorption capacity" within 1 minute. Preferably, "rapid absorption" hydrophilic polymers reach half maximal absorption capacity with 10 seconds and, more preferably, within 5 seconds. A study demonstrating that exemplary hydrophilic polymers have rapid absorption rates for saline is set forth in Example 8.

Fluid absorption can be accompanied by polymer swelling. In one embodiment, hydrophilic polymers swell in water to at least about 10 times their original volume. In a variation of this embodiment, hydrophilic polymers swell to at least about 20, and preferably at least about 50, times their original volume. In further variations of these embodiments, such swelling generally does not exceed 2000 times the original polymer volume.

In one embodiment, the hydrophilic polymer is a HIPE polymer that is characterized by a unique structure similar to that of the HIPE polymers described by Barby (U.S. Pat. No. 4,522,953, issued Jun. 11, 1985) and others. More specifically, hydrophilic HIPE polymers described herein have substantially spherical thin-walled cavities comprising a plurality of pores in the walls separating adjacent cavities (hereinafter termed a "HIPE-like structure"). In a variation of this embodiment, some cavities comprise six pores. Depending on the specific components and process conditions used in producing the polymers, this HIPE-like structure can be retained, to varying degrees, when the hydrophilic HIPE polymers are dried. For example, chemically stiffened HIPE polymers retain their HIPE-like structure upon drying.

The nominal void volume of hydrophilic HIPE polymers is generally about 70% to about 99%, more preferably about 75% to about 95%, and most preferably about 80% to about 90%.

The bulk density of chemically stiffened hydrophilic HIPE polymers typically ranges from about 0.01 gm/mL to about 0.8 gm/mL and is preferably between about 0.05 gm/mL and 0.25 gm/mL.

To reduce the shrinkage and/or deformation of polymer structure that can occur upon drying HIPE polymers, crosslinking is generally at least about 2%, usually at least about 5%, preferably at least about 10%, more preferably at least about 20%, and most preferably at least about 30%. Crosslinking usually does not exceed 50%.

Hydrophilic HIPE polymers can be produced that swell in water to at least about 100 times their original volume. In one embodiment, hydrophilic HIPE polymers swell to at least about 200, and preferably at least about 500, times their original volume. In one embodiment, such swelling generally does not exceed 2000 times the original volume.

When hydrophilic polymers (including hydrophilic HIPE polymers) are produced in the form of microbeads, the average diameter of the microbeads typically ranges from about 5 $\mu$m to about 1 cm in the dry state. Preferred average diameters range from about 50 $\mu$m to about 10 mm. In one embodiment, the average diameter does not exceed about 500 $\mu$m. This small size facilitates efficient washing of the microbeads to remove residual unpolymerized emulsion components. Also, the microbeads typically have a relatively uniform size and shape, which allows the wash conditions to be optimized to ensure that each microbead in a batch has been thoroughly washed. This feature facilitates cost-efficient scale-up of polymer production.

Hydrophilic Polymer Production

Hydrophilic polymers are conveniently produced from an emulsion of an oil discontinuous phase in a monomer-containing hydrophilic continuous phase. Such emulsions are polymerized directly to produce hydrophilic blocks or added to an oil suspension medium to form a suspension of emulsion droplets. Polymerization then converts the liquid emulsion droplets to solid microbeads. In one embodiment, the emulsion is a HIPE.

Components of the Emulsion

The hydrophilic monomer phase of the emulsion is conveniently an aqueous phase, as exemplified herein. However, those skilled in the art understand that other types of hydrophilic monomer phases are possible.

The hydrophilic monomer phase comprises a monomer, a crosslinker, an emulsifier, and a stabilizer. The monomer can be any hydrophilic, monofunctional monomer. Examples of suitable hydrophilic monomers include vinyl monomers having a polymerizable unsaturated group, such as an olefin unsaturated carboxylic acid, an olefin unsaturated sulfonic acid, an olefin unsaturated amine, and an olefin unsaturated ether.

Suitable vinyl monomers having unsaturated sulfonic acid groups include, for example, acryl amido methyl propane sulfonic acid and allyl sulfonic acid. An exemplary vinyl monomer having an unsaturated amino group is dimethyl aminoethyl methacrylate. Suitable vinyl monomers having unsaturated carboxyl groups include, for example, acrylic acid, methacrylic acid, maleic acid, and fumaric acid; and examples of suitable vinyl monomers having unsaturated carboxylate groups include acrylate, methacrylate, hydroxyethylmethacrylate, diethylaminoethyl methacrylate, hydroxyethylacrylate, diethylaminoethylacrylate, malate, fumarate, methoxypolyethyleneglycol methacrylate, and phenoxypolyethyleneglycol methacrylate.

Water-soluble salts of unsaturated carboxylic acids can also be employed in the present method. Suitable water-soluble salts include, for example, alkaline metal salts, alkaline earth metal salts, and ammonium salts of acrylic acid, methacrylic acid, acrylic methacrylic acid, and the like. Other examples of suitable hydrophilic monomers include vinyl pyridines, vinylpyrrolidones, acrylamide, methacrylamide, N-methylmethacrylamide, N-acryloylmorpholine, N-vinyl-N-methacetamide, and derivatives thereof.

A single monomer type or a mixture of types can be employed in the emulsion. For example, hydrophobic monomers that are copolymerizable with the hydrophilic monomers can also be employed in combination with hydrophilic monomers, although preferably the amount of hydrophobic monomer used does not exceed 50% by weight of total polymerizable monomer. Preferred monomers include acrylic acid, an acrylic acid salt, hydroxyethylacrylate, hydroxyethyl-methacrylate, acrylamide, and their derivatives.

The monomer concentration is generally in the range of about 0.5 to about 30 weight percent of the emulsion and is preferably about 5 weight percent to about 20 weight percent.

The crosslinker can be selected from a wide variety of polyfunctional monomers that are hydrophilic and/or at least partially soluble in the monomer component of the emulsion. For a crosslinker that is partially soluble in the monomer component, at least about 50% of the crosslinker dissolved in a 50:50 mixture of hydrophilic monomer and oil discontinuous phase partitions into the hydrophilic monomer phase when the mixture is allowed to separate into two phases. In one embodiment, the crosslinker is difunctional.

Suitable crosslinkers include, for example, polyallyl compounds, such as N,N'-diallyl acrylamide, diallylamine, diallyl methacrylamide, diallylamine diallylmethacrylamide, diallyl phthalate, diallyl malate, diallyl phosphate, diallyl terephthalate, N,N'-diallyltartardiamide, triallylcitrate, triallyl cyanurate, and triallyl phosphate; polyvinyl compounds, such as divinylbenzene, divinyl sulfone, ethylene glycol divinylethers (e.g., diethylene glycol divinylether), N,N'-methylene-bis-acrylamide, piperazine diacrylamide, N,N'-dihydroxyethylene-bis-acrylamide, ethylene glycol acrylates (e.g., ethylene glycol di-, tri-, and tetra-acrylate), ethylene glycol methacrylates (e.g., ethylene glycol di-, tri-, and tetra-methacrylate), glycerin trimethacrylate; hydroxyvinyl compounds, such as hydroxyethylacrylate, 2-hydroxyethyl methacrylate; and inorganic salts or organic metal salts that generate polyhydric ions such as calcium, magnesium, zinc, and aluminum. N,N'-bis-acrylylcystamine and the like are also suitable for use in producing hydrophilic polymers.

A single crosslinker type or a mixture of types can be employed in the emulsion. Preferably, the crosslinker is N,N'-methylene-bis-acrylamide, divinyl sulfone, diethylene glycol divinylether, or ethylene glycol diacrylate.

The crosslinker concentration is generally in the range of about 0.005 to about 30 weight percent of the emulsion and is preferably about 1 weight percent to about 10 weight percent. To reduce microbead shrinkage and/or deformation upon drying, the crosslinker is typically at least about 2 weight percent, and preferably at least about 5 weight percent, of total polymerizable monomer. When producing hydrophilic HIPE microbeads, the crosslinker is generally at least about 2 weight percent, usually at least about 5 weight percent, preferably at least about 10 weight percent, more preferably at least about 20 weight percent, and most preferably at least about 30 weight percent, of total polymerizable monomer. In general, the crosslinker does not exceed 50 weight percent of total polymerizable monomer.

The hydrophilic monomer phase also includes an emulsifier that promotes the formation of a stable emulsion. A suitable emulsifier has a hydrophobic cyclic head group and a hydrophilic tail. The hydrophobic cyclic head group preferably includes between 3 and about 7 carbon atoms and is selected to provide sufficient rigidity at the hydrophobic end of the molecule to reduce the tendency of the emulsion to reverse (i.e., the tendency of the oil discontinuous phase to become the continuous phase). For instance, the head group can be a cyclic group with multiple hydrophobic groups, such as, for example, alkyls, cyclic hydrocarbon groups, and aromatic groups. Preferably, the head group does not include hydrophilic groups, such as, for example, ionic groups including oxygen, nitrogen, and sulfur. In one embodiment, the head group consists of carbon and hydrogen atoms.

Examples of suitable emulsifiers include sugar fatty acid esters, such as distearate, and alkylaryl polyether alcohols, such as the Triton™ X series of nonionic surfactants commercially available from Union Carbide (Danbury, Conn.). The Triton™ X surfactants are mixtures with respect to the length of the polyoxyethylene chain, and the distribution of chain lengths follows the Poisson distribution. Generally, an alkylaryl polyether alcohol preparation suitable for use in producing the hydrophilic polymers described herein has an average number of ethylene oxide units per ether side chain of about 14 or more. Surprisingly good results are obtained when an alkylaryl polyether alcohol preparation having an average of at least about 30 ethylene oxide units per ether side chain (sold as Triton™ X-405) is employed as the emulsifier. The examples describe the use of Triton™ X-405 and X-705 (the latter has an average of 70 ethylene oxide units per ether side chain). The emulsifier can be a single type of emulsifier or a mixture of different types.

Sufficient emulsifier is employed to promote the formation of a stable emulsion. Generally, the emulsifier concentration is in the range of about 1 to about 30 weight percent of the emulsion; preferably, about 1 to about 20 weight percent; and more preferably, about 1 to about 5 weight percent.

The hydrophilic monomer phase also includes a stabilizer that reduces loss of the oil discontinuous phase from the emulsion and helps prevent coalescence. When producing hydrophilic polymers in microbead form, a suitable stabilizer is capable of forming a boundary between the oil discontinuous phase of the emulsion and the oil suspension medium where these two media interface in the microdroplet suspension. This phenomenon is analogous to the situation in soap bubbles where a boundary formed by detergent molecules separates air on the inside of the bubble from outside air.

The stabilizer can be a film-forming compound that is soluble in the hydrophilic monomer phase and sufficiently hydrophobic to stabilize the interface with the oil discontinuous phase of the emulsion. When producing microbeads, the stabilizer also stabilizes the interface between the oil discontinuous phase of the emulsion and the oil suspension medium. Suitable stabilizers act by forming a continuous film by entanglement of relatively strong polymer chains. Stabilizers useful in this regard include polymeric film formers for the interface between the hydrophilic monomer phase of the emulsion and the oil phase(s). These characteristics are found in a variety of natural and synthetic polymers, such as cellulose derivatives, polyacrylates (e.g., polyacrylic acid and polymethacrylic acid), polyalkylene glycols (e.g., polyethylene glycol), partially hydrolyzed polyvinyl alcohol (PVA, e.g., less than about 70–80% hydrolysis) and other polyols, guar gum, and agar gum. Also suitable for use as the stabilizer are copolymers of ethylenically unsaturated monomers, such as malein polybutadiene, malein polyethylene, and malein polyalpha-olefin.

Cellulose derivatives are generally preferred, and examples of suitable cellulose derivatives include methyl cellulose, hydroxymethyl cellulose, hydroxyethyl cellulose, ethylhydroxyethyl cellulose, hydroxypropyl cellulose, and other cellulose ethers, as well as cellulose esters, such as cellulose acetate, cellulose butylate, and cellulose acetate butylate. Other suitable stabilizers can be determined empirically by those skilled in the art in accordance with the teachings herein. The stabilizer employed can be a single type of stabilizer or a mixture of different types. Preferably, the stabilizer is methyl cellulose, hydroxyethyl cellulose, or PVA, with methyl cellulose being more preferred.

The stabilizer is employed in a concentration sufficient to reduce the loss of oil discontinuous phase from the emulsion droplets and to reduce microdroplet coalescence. Optimal concentrations vary with emulsion composition and are determined empirically. Generally, suitable stabilizer concentrations range from about 0.001 to about 2 weight percent of the emulsion. Higher stabilizer concentrations can be employed; however, at concentrations above 2 weight percent, the stabilizer can be difficult to wash out of the polymerized microbeads. Preferably, the stabilizer concentration is about 0.001 to about 1 weight percent of the emulsion and more preferably about 0.001 to about 0.7 weight percent.

If the stabilizer is obtained as a solid, the stabilizer is typically dissolved in an aqueous solvent (preferably, water), and this stabilizer solution is added to the hydrophilic monomer phase. Solutions containing between about 1 to about 5 weight percent stabilizer in water are conveniently employed, and solutions containing about 1 to about 2 weight percent stabilizer in water are preferred.

In addition to the foregoing, the hydrophilic monomer phase typically contains a hydrophilic polymerization initiator. As used to describe the polymerization initiator, the term "hydrophilic" means that an insubstantial amount of the polymerization initiator partitions into the oil discontinuous phase or the oil suspension medium so that less than about 5% of total polymerizable monomer is polymerized in an oil phase. The use of a hydrophilic initiator favors suspension polymerization over emulsion polymerization, thereby minimizing the formation of unwanted small (e.g., 100 Å) "emulsion particles."

The polymerization initiator can be any hydrophilic initiator that permits the formation of a stable emulsion. In general, the polymerization initiator is selected so that polymerization can be carried out at a temperature in the range of 15° C. to about 95° C., provided the temperature is lower than the boiling points of the emulsion components and, when producing hydrophilic microbeads, the components of the oil suspension medium. Furthermore, because emulsions according to the invention tend to be less stable at temperatures above 85° C., polymerization initiators that are effective at temperatures below about 85° C., and preferably below about 60° C., are typically employed. A polymerization initiator is considered "effective" if conversion of emulsion droplets to microbeads is complete within about 2 days. Preferably, this conversion is complete within about 2 to about 24 hours and more preferably within about 10 hours.

Examples of suitable initiators include hydrophilic initiators, such as sodium, potassium, and ammonium persulfates and perchlorates; sodium peracetate; sodium percarbonate; hydrogen peroxide; water-soluble azo initiators (e.g., 2,2'-azobis(2-amidinopropane) dihydrochloride, which is commercially available as V-50™ from Wako Chemicals, Inc., Richmond, Va.); and the like. A preferred initiator is ammonium persulfate.

The amount of initiator employed can vary depending on the desired rate of polymerization. The initiator concentration is generally in the range of about 0.01 to about 10 weight percent of total polymerizable monomer and is preferably in the range of about 0.01 weight percent to about 5 weight percent.

Initiators can be employed alone or in combination with other initiators, reducing agents, and/or catalysts. Reducing agents and catalysts useful in redox polymerization systems are well known, and the selection of a particular reducing agent or catalyst for a given initiator is within the level of skill in the art. Typically, any reducing agent and/or catalyst employed is at least partially soluble in the hydrophilic monomer phase.

Examples of reducing agents useful in redox systems include ferrous iron, bisulfites, thiosulfates, and various reducing sugars and amines. Conveniently, sodium hydrosulfite and/or N,N,N',N'-tetramethylenediamine (TEMED; available commercially as a 10% solution in water from Sigma Chemical Company, St. Louis, Mo.) is employed as the reducing agent.

Exemplary catalysts useful in conjunction with peroxides, persulfates, and other free radical generators include ferric iron complexes, such as iron (III) chloride hexahydrate, and complexes of other heavy metals (e.g., cobalt). Ferric iron complexes are typically used in combination with a reducing agent. An exemplary catalyst-reducing agent combination is iron (III) hexahydrate and sodium hydrosulfite, and other reducing agents or catalysts, such as TEMED, can be added to this combination.

The concentration of reducing agent and/or catalyst varies depending on the desired rate of polymerization. Typical reducing agent/catalyst concentrations range from about 0.01 gram/gram of initiator to about 2.0 gram/gram of initiator, and preferred concentrations can be determined empirically.

Reducing agents or catalysts are typically introduced when polymerization initiation is desired, i.e., generally after the emulsion has been formed. As discussed further below, reducing agents or catalysts are conveniently added directly to the emulsion when producing hydrophilic blocks and, when producing microbeads, to the oil suspension medium after formation of a microdroplet suspension.

The hydrophilic monomer phase can also include a hydrophilic solvent, which can be used to dissolve any emulsion components that are obtained in solid form or to increase the volume of the hydrophilic monomer phase. When the hydrophilic monomer phase is an aqueous phase, water is conveniently employed as the hydrophilic solvent.

In addition to the hydrophilic monomer phase, the emulsion contains an oil discontinuous phase, which can include any of a wide variety of well-known organic solvents that are immiscible with the hydrophilic monomer phase. Examples of suitable organic solvents include aliphatic hydrocarbons, such as n-pentane, cyclopentane, n-hexane, cyclohexane, n-heptane, and methylcyclohexane; aryl hydrocarbons, such as benzene, toluene, and xylene; and halogenated hydrocarbons, such as dichloromethane, dichloroethane, and trichloroethane; and the like. A preferred organic solvent for the oil discontinuous phase is toluene.

The amount of oil discontinuous phase in the emulsion is one of the important determinants of the physical properties of the hydrophilic polymer. In particular, the amount of oil discontinuous phase affects the void volume, density, cavity size, and surface area of the hydrophilic polymer produced upon polymerization. The weight percentage of oil discontinuous phase can be about 10%, about 20%, about 30%, about 40%, about 50%, or about 60% of the emulsion, and as high as about 99% of the emulsion. In one embodiment, the emulsion is a HIPE, and the weight percentage of oil discontinuous phase is generally in the range of about 70% to about 99%, more preferably about 75% to about 95%, and most preferably about 80% to about 90%.

Components of the Oil Suspension Medium Used in Producing Hydrophilic Microbeads If the hydrophilic polymer is to be produced in microbead form, the emulsion is added to an oil suspension medium to form a suspension of emulsion droplets. Typically, between about 0.5 and about 10 volumes of oil suspension medium per 1 volume of emulsion is used. The oil suspension medium generally includes an organic solvent that is immiscible with the hydrophilic monomer phase. The organic solvent can be an aliphatic, aromatic, halogenated, or other hydrocarbon solvent. Examples include the exemplary organic solvents discussed above as suitable for use in the oil discontinuous phase of the emulsion.

Typically, the oil suspension medium also includes a suspending agent. The suspending agent can be any agent or combination of agents that promotes the formation of a stable microdroplet suspension. Suitable suspending agents include oil-soluble natural and synthetic polymers such as for example cellulose and cellulose derivatives, polyacrylates (e.g., polymethacrylate), and ethylene oxide polymers. Preferably, ethyl cellulose is employed as the suspending agent. The suspending agent can be present in the oil suspension medium in any concentration that promotes the formation of a stable suspension, usually about 0.01 to about 10 weight percent of the oil suspension medium and preferably about 0.05 weight percent to about 3 weight percent.

Production of an Emulsion

The first step in the production of a hydrophilic polymer is the formation of an emulsion. Briefly, an emulsion is formed by preparing the hydrophilic monomer phase and the oil discontinuous phase and combining these phases while subjecting the mixture to shear agitation. Generally, a mixing or agitation device such as a pin impeller is used. The extent and duration of shear agitation must be sufficient to form a stable emulsion.

In addition, the degree of shear agitation is an important determinant of cavity size. While those skilled in the art understand that cavity size is influenced by a variety of factors (such as the components in the oil discontinuous phase and the type and quantity of suspending agent(s) in the oil suspension medium), shear agitation is generally inversely related to cavity size (all other factors being equal). Thus, the agitation can be increased or decreased to obtain a microbead with smaller or larger cavities, respectively.

In one embodiment, the emulsion is a HIPE. As described in the examples, a HIPE can be prepared using a Gifford-Wood Homogenizer-Mixer (Model 1-LV), set at 1400 rpm. At this mixing speed, the HIPE is produced in a few minutes. In another embodiment, a HIPE is prepared using an air-powered version of the above mixer (Model 1-LAV), with air pressure set at 5–10 psi for approximately 5–10 minutes. HIPEs according to the present invention can also be formed in a batchwise or continuous process, such as that disclosed in U.S. Pat. No. 5,149,720 (DesMarais et al., issued Sep. 22, 1992).

Polymerization of the Emulsion to Produce a Hydrophilic Block

To produce a hydrophilic block, polymerization can be initiated by increasing the temperature of the emulsion above ambient temperature and/or by adding one or more reducing agents or catalysts to the emulsion. Polymerization conditions vary depending upon the composition of the emulsion. For example, the monomer or monomer mixture and the polymerization initiator(s) are particularly important determinants of polymerization temperature. Furthermore, the conditions are selected such that a stable emulsion can be maintained for the length of time necessary for polymerization. In particular, polymerization is typically carried out at a temperature that is lower than the boiling points of the emulsion components and low enough to avoid breaking of the emulsion. The determination of a suitable polymerization temperature for a given emulsion is within the level of skill in the art. As stated above, the temperature of the emulsion should generally not be elevated above about 95° C., and is preferably less than about 85° C., and more preferably less than about 60° C.

Polymerization can also be initiated chemically by using one or more reducing agents or catalysts. When producing a hydrophilic block, the reducing agent(s) and/or catalyst(s) is/are added to the emulsion. Suitable concentrations for, and combinations of, reducing agents and catalysts are described above.

Production and Polymerization of an Emulsion Droplet Suspension to Produce Hydrophilic Microbeads If hydrophilic microbeads are desired, the emulsion is added to an oil suspension medium prior to polymerization.

The emulsion must be added to the suspension medium in an amount and at a rate suitable for forming a suspension of emulsion droplets. Typically, between about 0.1 to about 2 volumes of emulsion are added to one volume of suspension medium. The emulsion is preferably added in the presence of an inert gas, such as nitrogen, to reduce the likelihood of polymerization beginning before a stable suspension is established. As the emulsion is added, the suspension is subjected to sufficient shear agitation to form a stable suspension. To ensure that the microbeads produced are relatively uniform in size, the mixing device used should provide a relatively uniform distribution of agitation force throughout the suspension.

Droplet size is influenced by the degree of shear agitation along with the type and quantity of the suspending agent and the temperature and viscosity of the oil suspension medium. All other factors being equal, however, shear agitation is generally inversely related to droplet size. Therefore, the agitation can be increased or decreased to obtain smaller or larger emulsion droplets, respectively. Thus, the degree of shear agitation can be adjusted to adjust the size of the microbead produced upon polymerization.

To produce a stable suspension in a 2-liter spherical reactor having baffles or indents, for example, the emulsion can be added to the suspension medium dropwise at a flow rate of up to about 500 ml/minute. Agitation can range from about 50 to about 1500 rpm and is preferably from about 250 to about 500 rpm when a propeller- or paddle-style impeller with a diameter of approximately 1.5 to 3 inches is used.

Polymerization is initiated by increasing the temperature of the suspension above ambient temperature and/or by adding one or more reducing agents or catalysts to the oil suspension medium. The considerations relating to the thermal or chemical initiation of polymerization are as described above, except that the initiation conditions (i.e., temperature, reducing agent and/or catalyst type and concentration) are generally selected to ensure the stability of the suspension, as well as the stability of the emulsion. The selection of suitable initiation conditions for polymerizing a suspension of emulsion droplets is within the level of skill in the art in light of the teachings herein.

Washing and Drying of Hydrophilic Polymers

The polymerization step converts the emulsion to solid hydrophilic polymer. In the case of a suspended emulsion, droplets are converted to hydrophilic microbeads. As discussed above, the hydrophilic polymer is generally washed to remove any residual unpolymerized components. Hydrophilic polymers can be washed with any liquid that can solubilize the residual components without affecting polymer stability. Generally, water is not used for washing hydrophilic polymers because of their high water absorption capacity. More than one cycle of washing may be required. Preferably, hydrophilic polymers are extracted with acetone for roughly a day in a Soxhlet extractor, followed by Soxhlet extraction with methanol for about a day. The polymers can then be dried in any conventional manner, such as, for example, air-drying for two days or drying under vacuum at about 50–60° C. overnight.

In one embodiment, a hydrophilic polymer is subjected to "chemical stiffening" to reduce deformation upon drying. Chemical stiffening is generally carried out by treating the hydrophilic polymer with a hydrophilic solvent prior to drying. The hydrophilic solvent is one that can substantially replace any water in the hydrophilic polymer. Accordingly, the hydrophilic solvent is itself preferably substantially free of water. Alcohols, such as methanol or isopropanol, are conveniently employed for this purpose, with methanol being preferred.

A hydrophilic block can be treated with a hydrophilic solvent by immersing the block in the solvent for a time sufficient to allow the solvent to penetrate the block. For a cylindrical block of, e.g., about 5 cm in diameter by about 4 cm long, immersing in solvent overnight is generally sufficient. The solvent can then be expelled by any convenient method, such as by gentle squeezing. In one embodiment, this process is carried out with methanol and repeated with acetone, followed by another methanol treatment. After treatment with a hydrophilic solvent, the hydrophilic block is dried as discussed above.

To produce chemically stiffened hydrophilic microbeads, the hydrophilic microbeads are collected after polymerization by precipitation, decantation, or filtration. Conveniently, microbeads are collected by precipitation using the hydrophilic solvent employed for chemical stiffening. Accordingly, the hydrophilic solvent is added to the microbeads/oil suspension medium mixture in an amount sufficient to precipitate substantially all (i.e., 90%) of the microbeads. For example, 2 volumes of methanol added to 1 volume of microbeads/oil suspension medium is generally sufficient for this purpose. Once collected, the microbeads are washed at least once with the hydrophilic solvent. Soxhlet extraction using acetone followed by methanol can then be carried out as described above, and the microbeads are dried also as described above.

This chemical stiffening step is unexpectedly effective at helping to preserve the porous structure that characterizes the hydrophilic polymer immediately after polymerization. In particular, this step can be employed when hydrophilic HIPE polymer having a HIPE-like structure in the dry state is desired. Although some shrinkage typically occurs as the wet polymer is dried, chemical stiffening helps reduce deformation of the pore structure and associated loss of porosity.

Uses of Hydrophilic Polymers

The hydrophilic polymers described herein are useful for a variety of applications, notably, as an absorbent material and as a solid support in biotechnology applications. Hydrophilic polymers can be used, for example, to absorb bodily fluids (e.g., in diapers, sanitary napkins, tampons, and wound dressings); to absorb or transport solvents or other chemicals; and as a scavenger of, e.g., aqueous fluids. Hydrophilic polymer absorbents can also be employed to help control debris flows triggered by heavy rains and/or flooding.

Biotechnology applications include filtration; chromatographic separation, such as for example ion exchange; solid-phase synthesis; and immobilization of agents such as antibodies or enzymes. Other utilities are apparent to those familiar with polymeric materials, including, for example, use in adhesives, paper, and insulation.

Hydrophilic polymers, especially hydrophilic microbeads, can be used as carriers to provide sustained release of an agent, such as a fragrance, a cosmetic, an insecticide, a fertilizer, or water (e.g., in agricultural applications). Hydrophilic microbeads are especially well-suited for use as drug microcarriers, as such microbeads tend to be distributed throughout the body and can be produced in a biodegradable form more easily than hydrophobic microbeads. Hydrophilic microbeads are also well-suited for use in microbial and mammalian cell culture.

Many of the physical characteristics of hydrophilic polymers, such as void volume and cavity size, are relatively controllable. Therefore, different types of hydrophilic polymers, having physical characteristics tailored for different uses, can be produced. The high void volume of hydrophilic HIPE polymers, for example, provides exceptional absorbency. Furthermore, because the interconnectedness of the cavities in hydrophilic HIPE polymers allows liquids to flow through the polymer material, hydrophilic HIPE polymers serve as excellent substrates for use in biotechnology applications such as chromatographic separation of proteins and peptide synthesis.

Because the polymers of the invention are naturally hydrophilic, the polymers are useful in many of the above applications without further modification. However, those skilled in the art will appreciate that hydrophilic polymers specialized for particular applications can readily be produced. In particular, specialized polymers can be produced directly by polymerizing monomers and crosslinkers having desired properties or indirectly by modifying polymers after polymerization. Hydrophilic polymers functionalized for absorption of specific liquids, for example, can be prepared by chemical modification of preformed hydrophilic polymers bearing a reactive group, such as a hydroxyl, a sulfonic group (e.g., a sulfan), a carboxylic group, an amine, or an epoxy group.

All publications referred to herein are expressly incorporated by reference in their entirety as indicative of the level of skill in the art.

This invention is further illustrated by the following specific but non-limiting examples. Procedures that are constructively reduced to practice are described in the present tense, and procedures that have been carried out in the laboratory are set forth in the past tense. Unless otherwise indicated, concentrations expressed as percentages are percentages by weight.

EXAMPLE 1

Preparation of Hydrophilic Microbeads

Hydrophilic microbeads were prepared from a suspension of a HIPE including a hydrophilic monomer phase and an oil discontinuous phase. The components and amounts used in this study are indicated in Table 1. The pH of the acrylic acid was adjusted to about 5.0 using a 25% solution of sodium hydroxide (25% NaOH). The components of the hydrophilic monomer phase where mixed in a 1-liter beaker by stirring at room temperature. The beaker was placed under a Gifford-Wood Homogenizer-Mixer (Model 1-LV; commercially available from Greerco, Hudson, N.H.), and the hydrophilic monomer phase was stirred at 1500 rpm while slowly adding 300 ml toluene to form a HIPE.

An oil suspension medium containing 2% ethyl cellulose (48% substituted) in dichloromethane was prepared, and 450 ml was added to a 2-liter reactor and stirred at 200 rpm under a nitrogen gas stream at room temperature for about 15 minutes (mins). The HIPE was added to the oil suspension medium dropwise at a flow rate of approximately 200 ml/min. The nitrogen stream was continued during the addition of the HIPE and about 10 mins thereafter.

The stirring speed was adjusted to 176 rpm, and polymerization was initiated by adding aqueous solutions of sodium hydrosulfite and iron (III) chloride hexahydrate. Polymerization was initiated at 22.5° C., and the temperature rose as high as 32° C. Polymerization was allowed to continue for 20 hours (hrs).

Two volumes of methanol were added to the resultant microbead/oil suspension medium mixture, thereby precipitating the hydrophilic microbeads. The hydrophilic microbeads were washed once with methanol and extracted with acetone followed by methanol in a Soxhlet extractor for approximately 18 hours each. The microbeads were allowed to air-dry overnight.

The microbeads were 2.44% crosslinked and had a bulk density of 0.220 gm/mL. The microbeads swelled in water to more than 500 times their dry volume.

TABLE 1

| | Amount | Weight % in HIPE |
|---|---|---|
| HIPE | | |
| Acrylic acid, pH = 5.0 | 20.0 gm | 5.27 |
| N,N'-methylene-bis-acrylamide | 0.5 gm | 0.13 |
| Triton ™ X-405 | 8.0 mL | 2.11 |
| APS* | 0.71 gm | 0.19 |
| PVA (< about 70% hydrolysis; 1% in water) | 50.0 mL | 13.19 |
| Toluene | 300.0 mL | 79.11 |
| Total | 379.21 | 100.00 |
| Oil Suspension Medium | | |
| Dichloromethane, 2% Ethyl cellulose (48% substituted) | 450.0 mL | |
| Sodium hydrosulfite (0.1 gm/mL in water) | 0.1 gm | |
| Iron (III) chloride hexahydrate (0.1 gm/mL in water) | 0.1 gm | |
| Temperature | 22.5° C. | |
| Suspension stirring speed | 176 rpm | |
| Time | 20 hrs | |

*Ammonium persulfate

EXAMPLE 2 (COMPARATIVE EXAMPLE)

Polymerization of Suspended Hydrophilic Monomer Phase Droplets

This example describes the preparation of microbeads from a suspension of a hydrophilic monomer phase in an oil suspension medium. A comparison of this example with Example 1 illustrates the differences between polymerization of a "water-in-oil"-type suspension (this example) and polymerization of an "oil-in-water-in-oil"-type suspension (Example 1).

The components and amounts used in this study are indicated in Table 2. A hydrophilic monomer phase was prepared in a 1-liter beaker as described in Example 1. An oil suspension medium containing 2% ethyl cellulose (48% substituted) in dichloromethane was prepared, and 450 ml was added to a 2-liter reactor and stirred at 200 rpm. The hydrophilic monomer phase was added to the oil suspension medium as described for the HIPE in Example 1, and the remainder of the process was carried out as described in Example 1.

The resultant hydrophilic microbeads were 2.44% crosslinked and swelled in water to approximately ten times their dry volume.

TABLE 2

| | Amount | Weight % of AMS |
|---|---|---|
| Hydrophilic Monomer Phase | | |
| Acrylic acid, pH = 5.0 | 20.0 gm | 25.25 |
| N,N'-methylene-bis-acrylamide | 0.5 gm | 0.63 |
| Triton ™ X-405 | 8.0 mL | 10.10 |
| APS | 0.71 gm | 0.90 |
| 1% Methyl cellulose in water | 50.0 mL | 63.12 |
| Total | 79.21 | 100.00 |

TABLE 2-continued

|  | Amount | Weight % of AMS |
|---|---|---|
| Oil Suspension Medium | | |
| Dichloromethane, 2% Ethyl cellulose (48% substituted) | 450.0 mL | |
| Sodium hydrosulfite (0.1 gm/mL in water) | 0.1 gm | |
| Iron(III) chloride hexahydrate (0.1 gm/mL in water) | 0.1 gm | |
| Temperature | 22.5° C. | |
| Suspension stirring speed | 176 rpm | |
| Time | 20 hrs | |

EXAMPLE 3

Exemplary preferred microbeads were prepared according to the following general protocol. The details of specific studies are set forth in Tables 3–16.

1. In a 1-liter beaker, prepare an hydrophilic monomer phase by mixing a hydrophilic monomer, a hydrophilic or monomer-soluble crosslinker, an emulsifier, a hydrophilic initiator, and a solution of stabilizer in water. If acrylic acid is used as the monomer, adjust the pH of the acrylic acid to about 5.0 (i.e., between 4.6 and 6.0) using 25% NaOH prior to mixing with the other components. Mix by stirring at room temperature.

2. Place the beaker under a Gifford-Wood Homogenizer-Mixer (Model 1-LV; commercially available from Greerco, Hudson, N.H.) and stir at 1700 to 4800 rpm while slowly adding an organic solvent to form an emulsion.

3. In a 2-liter glass cylinder reactor (from Ace Glass, Vineland, N.J.), prepare an oil suspension medium by combining an organic solvent with a suspending agent. Stir under a nitrogen gas stream for about 15 mins at 50 to 1500 rpm at room temperature.

4. Add the emulsion to the oil suspension medium dropwise at a flow rate of approximately 200±50 ml/min under a nitrogen stream. Maintain the nitrogen stream for about 10 mins after the emulsion has been added.

5. Adjust the stirring speed, if necessary, to the desired suspension stirring speed.

6. To form microbeads, polymerize the suspension under constant stirring by raising the temperature or adding one or more reducing agents and/or catalysts to the suspension.

7. Collect the hydrophilic microbeads by precipitation, decantation, or filtration.

8. Wash the hydrophilic microbeads once with methanol, and then extract with acetone and then methanol in a Soxhlet extractor for approximately 18–24 hours each.

9. Allow the microbeads to air-dry overnight, or dry the microbeads in a vacuum oven at 60° C. for 10–16 hours.

TABLE 3

|  | Amount | Weight % of HIPE |
|---|---|---|
| HIPE | | |
| Acrylamide | 15.0 gm | 5.51 |
| N,N"-methylene-bis-acrylamide | 0.6 gm | 0.22 |
| Triton ™ X-405 | 6.0 mL | 2.21 |
| APS | 0.5 gm | 0.18 |
| 1% Methyl cellulose in water | 50.0 mL | 18.38 |
| Toluene | 200.0 mL | 73.50 |
| Total | 272.1 | 100.00 |
| Oil Suspension Medium | | |
| Dichloromethane | 450.0 mL | |
| Ethyl cellulose (48% substituted) | 25.0 gm | |
| TEMED | 0.8 mL | |
| Temperature | 21.2° C. | |
| Suspension stirring speed | 320 rpm | |
| Time | 6 hrs | |

The resultant microbeads were 3.85% crosslinked and had a bulk density of 0.222 gm/mL.

TABLE 4

|  | Amount | Weight % in HIPE |
|---|---|---|
| HIPE | | |
| Acrylic acid, pH = 5.0 | 30.0 gm | 5.76 |
| N-N'-methylene-bis-acrylamide | 0.25 gm | 0.05 |
| Triton ™ X-405 | 10.0 mL | 1.92 |
| APS | 0.5 gm | 0.10 |
| 1% Methyl cellulose in water | 80.0 mL | 15.36 |
| Toluene | 400.0 mL | 76.81 |
| Total | 520.75 | 100.00 |
| Oil Suspension Medium | | |
| Dichloromethane | 650.0 mL | |
| Ethyl cellulose (48% substituted) | 32.0 gm | |
| TEMED | 0.8 ml | |
| Temperature | 40° C. | |
| Suspension stirring speed | 160 rpm | |
| Time | 20 hrs | |

The resultant microbeads were 0.83% crosslinked.

TABLE 5

|  | Amount | Weight % in HIPE |
|---|---|---|
| HIPE | | |
| Acrylic acid, pH = 5.0 | 30.0 gm | 3.69 |
| Diethyleneglycol divinylether | 0.5 gm | 0.06 |
| Triton ™ X-405 | 11.0 mL | 1.35 |
| APS | 0.74 gm | 0.09 |
| 1% Methyl cellulose in water | 70.0 mL | 8.62 |
| Toluene | 700.0 mL | 86.18 |
| Total | 812.24 | 100.00 |
| Oil Suspension Medium | | |
| Dichloromethane | 1000.0 mL | |
| Ethyl cellulose (48% substituted; 4 centipoise) | 20.0 gm | |
| TEMED | 2.5 mL | |
| Temperature | 22° C. | |
| Suspension stirring speed | 170 rpm | |
| Time | 24 hrs | |

The resultant microbeads were 1.64% crosslinked.

TABLE 6

|  | Amount | Weight % in HIPE |
|---|---|---|
| HIPE | | |
| Acrylic acid, pH = 5.0 | 30.1 gm | 4.91 |
| Ethyleneglycol dimethacrylate | 0.52 gm | 0.08 |
| Triton ™ X-405 | 11.48 mL | 1.87 |
| APS | 0.67 gm | 0.11 |
| 1% Methyl cellulose in water | 70.0 mL | 11.42 |
| Toluene | 500.0 mL | 81.60 |
| Total | 612.77 | 100.00 |
| Oil Suspension Medium | | |
| Dichloromethane | 750.0 mL | |
| Ethyl cellulose (48% substituted) | 30.0 gm | |
| TEMED | 1.0 mL | |
| Sodium hydrosulfite | 0.1 gm | |
| Iron(III) chloride hexahydrate | 0.1 gm | |
| Temperature | 33° C. | |
| Suspension stirring speed | 257 rpm | |
| Time | 20 hrs | |

The resultant microbeads were 1.70% crosslinked.

TABLE 7

|  | Amount | Weight % in HIPE |
|---|---|---|
| HIPE | | |
| Acrylamide | 15.0 gm | 2.09 |
| N,N'-methylene-bis-acrylamide | 8.0 gm | 1.12 |
| Triton ™ X-405 | 13.0 mL | 1.81 |
| APS | 0.5 gm | 0.07 |
| 1% Methyl cellulose in water | 60.0 mL | 8.37 |
| Toluene | 620.0 mL | 86.53 |
| Total | 716.5 | 100.00 |
| Oil Suspension Medium | | |
| Dichloromethane | 800.0 mL | |
| Ethyl cellulose (48% substituted) | 40.0 gm | |
| TEMED | 0.8 mL | |
| Temperature | 18.5° C. | |
| Suspension Stirring speed | 196 rpm | |
| Time | 6 hrs | |

The resultant microbeads were 34.78% crosslinked and had a bulk density of about 0.125% gm/mL.

TABLE 8

|  | Amount | Weight % in HIPE |
|---|---|---|
| HIPE | | |
| Acrylamide | 10.0 gm | 2.69 |
| N,N'-methylene-bis-acrylamide | 1.5 gm | 0.40 |
| Triton ™ X-405 | 10.0 mL | 2.69 |
| APS | 0.5 gm | 0.13 |
| 1% Methyl cellulose in water | 50.0 mL | 13.44 |
| Toluene | 300.0 mL | 80.65 |
| Total | 372.0 | 100.00 |
| Oil Suspension Medium | | |
| Toluene | 350.0 mL | |
| Ethyl cellulose | 3.5 gm | |

TABLE 8-continued

|  | Amount | Weight % in HIPE |
|---|---|---|
| TEMED | 0.8 mL | |
| Temperature | 22.5° C. | |
| Suspension stirring speed | 320 rpm | |
| Time | overnight | |

The resultant microbeads were 13.04% crosslinked and had a bulk density of about 0.087% gm/mL.

TABLE 9

|  | Amount | Weight % in HIPE |
|---|---|---|
| HIPE | | |
| Acrylic acid, pH = 5.0 | 30.0 gm | 4.20 |
| N,N'-methylene-bis-acrylamide | 3.0 gm | 0.42 |
| Triton ™ X-705 | 10.0 mL | 1.40 |
| APS | 1.1 gm | 0.15 |
| 1% Methyl cellulose in water | 70.0 mL | 9.80 |
| Toluene | 600.0 mL | 84.02 |
| Total | 714.1 | 100.00 |
| Oil Suspension Medium | | |
| Dichloromethane | 1000.0 mL | |
| Ethyl cellulose (48% substituted) | 20.0 gm | |
| Sodium hydrosulfite | 0.1 gm | |
| Iron(III) chloride hexahydrate | 0.1 gm | |
| Temperature | 22.5° C. | |
| Suspension stirring speed | 160 rpm | |
| Time | overnight | |

The resultant microbeads were 9.09% crosslinked and had a bulk density of about 0.141% gm/mL.

TABLE 10

|  | Amount | Weight % in HIPE |
|---|---|---|
| HIPE | | |
| Acrylic acid, pH = 5.0 | 30.0 gm | 4.89 |
| Divinyl sulfone | 1.0 gm | 0.16 |
| Triton ™ X-405 | 12.0 mL | 1.95 |
| APS | 1.0 gm | 0.16 |
| PVA (1.4% in water) | 70.0 mL | 11.40 |
| Toluene | 500.0 mL | 81.43 |
| Total | 614.0 | 100.00 |
| Oil Suspension Medium | | |
| Trichloroethane | 1000.0 mL | |
| Ethyl cellulose (48% substituted; 4 centipoise) | 20.0 gm | |
| TEMED | 2.0 mL | |
| Temperature | 30.0° C. | |
| Suspension stirring speed | 190 rpm | |

The resultant microbeads were 3.23% crosslinked.

TABLE 11

| | Amount | Weight % in HIPE |
|---|---|---|
| HIPE | | |
| Acrylic acid, pH = 5.0 | 40.0 gm | 5.27 |
| N,N'-methylene-bis-acrylamide | 2.1 gm | 0.28 |
| Triton ™ X-405 | 16.0 mL | 2.11 |
| APS | 1.6 gm | 0.21 |
| 2% Methyl cellulose in water | 100.0 mL | 13.16 |
| Toluene | 600.0 mL | 78.98 |
| Total | 759.7 | 100.00 |
| Oil Suspension Medium | | |
| Dichloromethane, 2% Ethyl cellulose (48% substituted) | 950.0 mL | |
| Sodium hydrosulfite (0.1 gm/mL in water) | 0.1 gm | |
| Iron (III) chloride hexahydrate (0.1 gm/mL in water) | 0.1 gm | |
| Temperature | 22.5° C. | |
| Suspension stirring speed | 186 rpm | |
| Time | 6 hrs | |

The resultant microbeads were 4.99% crosslinked.

TABLE 12

| | Amount | Weight % in HIPE |
|---|---|---|
| HIPE | | |
| Acrylic acid, pH = 5.0 | 30.0 gm | 4.00 |
| N,N'-methylene-bis-acrylamide | 2.1 gm | 0.28 |
| Triton ™ X-405 | 16.0 mL | 2.13 |
| APS | 1.6 gm | 0.21 |
| 1% Methyl cellulose in water | 100.0 mL | 13.34 |
| Toluene | 600.0 mL | 80.03 |
| Total | 749.7 | 100.00 |
| Oil Suspension Medium | | |
| Dichloromethane, 2% Ethyl cellulose (48% substituted) | 1000.0 mL | |
| Sodium hydrosulfite (0.1 gm/mL in water) | 0.1 gm | |
| Iron (III) chloride hexahydrate (0.1 gm/mL in water) | 0.1 gm | |
| Temperature | 22.5° C. | |
| Suspension stirring speed | 186 rpm | |
| Time | 3 hrs | |

The resultant microbeads were 6.54% crosslinked.

TABLE 13

| | Amount | Weight % in HIPE |
|---|---|---|
| HIPE | | |
| Acrylic acid, pH = 5.0 | 20.0 gm | 2.56 |
| N,N'-methylene-bis-acrylamide | 10.0 gm | 1.28 |
| Triton ™ X-405 | 10.0 mL | 1.28 |
| APS | 0.71 gm | 0.09 |
| 1% Methyl cellulose in water | 40.0 mL | 5.12 |
| Toluene | 700.0 mL | 89.66 |
| Total | 780.71 | 100.00 |

TABLE 13-continued

| | Amount | Weight % in HIPE |
|---|---|---|
| Oil Suspension Medium | | |
| Dichloromethane | 1000.0 mL | |
| 2% Ethyl cellulose (48% substituted; 10 centipoise) | 20.0 gm | |
| TEMED | 3.0 mL | |
| Temperature | 38.0° C. | |
| Suspension stirring speed | 176 rpm | |

The resultant microbeads were 33.33% crosslinked.

TABLE 14

| | Amount | Weight % in HIPE |
|---|---|---|
| HIPE | | |
| Acrylic acid, pH = 5.0 | 30.0 gm | 4.17 |
| N,N'-methylene-bis-acrylamide | 2.5 gm | 0.35 |
| Triton ™ X-705 | 16.0 mL | 2.22 |
| APS | 1.1 gm | 0.15 |
| 1% Methyl cellulose in water | 70.0 mL | 9.73 |
| Toluene | 600.0 mL | 83.38 |
| Total | 719.6 | 100.00 |
| Oil Suspension Medium | | |
| Dichloromethane | 1000.0 mL | |
| 2% Ethyl cellulose (48% substituted) | 20.0 gm | |
| Sodium hydrosulfite (0.1 gm/mL in water) | 0.1 gm | |
| Iron (III) chloride hexahydrate (0.1 gm/mL in water) | 0.1 gm | |
| Temperature | 22.5° C. | |
| Suspension stirring speed | 160 rpm | |
| Time | overnight | |

The resultant microbeads were 7.69% crosslinked.

TABLE 15

| | Amount | Weight % in HIPE |
|---|---|---|
| HIPE | | |
| Acrylic acid, pH = 5.0 | 30.0 gm | 4.20 |
| N,N'-methylene-bis-acrylamide | 3.0 gm | 0.42 |
| Triton ™ X-705 | 10.0 mL | 1.40 |
| APS | 1.1 gm | 0.15 |
| PVA (1% in water) | 70.0 mL | 9.80 |
| Toluene | 600.0 mL | 84.02 |
| Total | 714.1 | 100.00 |
| Oil Suspension Medium | | |
| Dichloromethane | 1000.0 mL | |
| 2% Ethyl cellulose (48% substituted) | 20.0 gm | |
| Sodium hydrosulfite (0.1 gm/mL in water) | 0.1 gm | |
| Iron (III) chloride hexahydrate (0.1 gm/mL in water) | 0.1 gm | |
| Temperature | 22.5° C. | |
| Suspension stirring speed | 160 rpm | |
| Time | overnight | |

The resultant microbeads were 9.09% crosslinked.

TABLE 16

|  | Amount | Weight % in HIPE |
|---|---|---|
| HIPE | | |
| Acrylic acid, pH = 5.0 | 20.0 gm | 2.47 |
| N,N'-methylene-bis-acrylamide | 7.0 gm | 0.87 |
| Triton ™ X-405 | 11.0 mL | 1.36 |
| APS | 0.71 gm | 0.09 |
| 1% Methyl cellulose in water | 70.0 mL | 8.66 |
| Toluene | 700.0 mL | 86.56 |
| Total | 808.71 | 100.00 |
| Oil Suspension Medium | | |
| Dichloromethane, 5% Ethyl cellulose (48% substituted; 4 centipoise) | 800.0 mL | |
| TEMED | 1.0 mL | |
| Temperature | 40.0° C. | |
| Suspension stirring speed | 176 rpm | |
| Time | 10 hrs | |

The resultant microbeads were 25.93% crosslinked.

EXAMPLE 4

Preparation of a Hydrophilic Block

A hydrophilic block was prepared from a HIPE as follows. The components and amounts used in this study are indicated in Table 17. The pH of the acrylic acid was adjusted to about 5.0 using 25%. NaOH. The components of the hydrophilic monomer phase where mixed in a 1-liter beaker by stirring at room temperature under a nitrogen gas stream. The beaker was placed under a Gifford-Wood Homogenizer-Mixer (Model 1-LV; commercially available from Greerco, Hudson, N.H.) and the hydrophilic monomer phase was stirred at 1700 rpm under nitrogen while slowly adding 600 ml toluene to form a HIPE. The nitrogen stream was discontinued about 10 mins after toluene addition was complete.

The HIPE was poured into a glass jar, and polymerization was initiated by heating the jar to 60° C. Polymerization was allowed to continue at this temperature for 20 hrs.

The resulting hydrophilic block was immersed in methanol overnight, and methanol was removed by gentle squeezing. This process was repeated with acetone. The hydrophilic block was then sliced thinly, soaked in methanol overnight, and dried in a vacuum oven at 60° C. for several hours. The HIPE block was 3.60% crosslinked.

TABLE 17

|  | Amount | Weight % of HIPE |
|---|---|---|
| HIPE | | |
| Acrylic acid, pH = 5.0 | 40.0 gm | 5.27 |
| N,N'-methylene-bis-acrylamide | 2.1 gm | 0.28 |
| Triton ™ X-405 | 16.0 mL | 2.11 |
| APS | 1.6 gm | 0.21 |
| 1% Methyl cellulose in water | 100.0 mL | 13.16 |
| Toluene | 600.0 mL | 78.98 |
| Total | 759.7 mL | 100.00 |
| Temperature | 60° C. | |
| Suspension stirring speed | 320 rpm | |
| Time | 6 hrs | |

EXAMPLE 5

Production and Sulfonation of Hydrophobic Microbeads

Polystyrene/divinylbeneze (DVB) microbeads were produced as described in Example 1B of International Application No. PCT/US95/06879 (WO 95/33553, published Dec. 14, 1995). Briefly, a HIPE including a monomer phase containing styrene and DVB and an aqueous discontinuous phase was suspended in an aqueous suspension medium. The components of these media are shown in Tables 18–24.

The resulting hydrophobic microbeads were sulfonated by soaking them in concentrated sulfuric acid at 60° C. overnight. The microbeads were washed with water, extracted methanol with for approximately 10 hrs in a Soxhlet extractor, and dried in a vacuum oven at 60° C. overnight. The sulfonated microbeads were then added to water. The capacity of the sulfonated microbeads was calculated by titrating the microbeads to pH 7.0 with 0.1 N NaOH. The microbeads were sulfonated to a capacity of 3.5 milliequivalents/wet gm polymer (milliequivalents were determined by multiplying the volume of the NaOH solution added by 0.1).

TABLE 18

|  | Amount | Weight % in HIPE |
|---|---|---|
| HIPE | | |
| Lauroyl peroxide | 10.5 gm | 0.12 |
| 1% Ethyl cellulose in trichloroethane | 100.0 mL | 1.15 |
| Toluene | 100.0 mL | 1.15 |
| Span ™ 80 | 160.2 gm | 1.84 |
| DVB (55%) | 21.0 gm | 0.24 |
| Styrene | 300.0 gm | 3.45 |
| Water | 8000.0 mL | 92.04 |
| Total | 8691.7 | 100.00 |
| Aqueous Suspension Medium | | |
| Water | 8000.0 mL | |
| Acacia | 1000.0 gm | |
| Temperature | 45.0° C. | |
| Suspension stirring speed | 300 rpm | |
| Time | 48 hrs | |

The resultant microbeads were 3.60% crosslinked.

TABLE 19

|  | Amount | Weight % in HIPE |
|---|---|---|
| HIPE | | |
| Lauroyl peroxide | 10.2 gm | 0.15 |
| 1% Ethyl cellulose in trichloroethane | 200.0 mL | 2.96 |
| Span ™ 80 | 158.8 gm | 2.35 |
| DVB (55%) | 350.0 gm | 5.18 |
| Styrene | 35.0 gm | 0.52 |
| Water | 6000.0 mL | 88.84 |
| Total | 6754.0 | 100.00 |
| Aqueous Suspension Medium | | |
| Water | 6000.0 mL | |
| Acacia | 900.0 gm | |
| Temperature | 45.0° C. | |
| Suspension stirring speed | 120 rpm | |
| Time | 48 hrs | |

The resultant microbeads were 50.00% crosslinked.

TABLE 20

|  | Amount | Weight % in HIPE |
|---|---|---|
| HIPE |  |  |
| Lauroyl peroxide | 10.5 gm | 0.12 |
| 1% Ethyl cellulose in trichloroethane | 100.0 mL | 1.13 |
| Toluene | 100.0 mL | 1.13 |
| Span ™ 80 | 160.2 gm | 1.80 |
| DVB (55%) | 10.0 gm | 0.11 |
| Styrene | 500.0 gm | 5.63 |
| Water | 8000.0 mL | 90.08 |
| Total | 8880.7 | 100.00 |
| Aqueous Suspension Medium |  |  |
| Water | 8000.0 mL |  |
| Acacia | 1000.0 gm |  |
| Temperature | 45.0° C. |  |
| Suspension stirring speed | 300 rpm |  |
| Time | 48 hrs |  |

The resultant microbeads were 1.08% crosslinked.

TABLE 21

|  | Amount | Weight % in HIPE |
|---|---|---|
| HIPE |  |  |
| Lauroyl peroxide | 10.5 gm | 0.12 |
| 1% Ethyl cellulose in trichloroethane | 200.0 mL | 2.27 |
| Span ™ 80 | 162.0 gm | 1.84 |
| DVB (55%) | 45.0 gm | 0.51 |
| Styrene | 380.0 gm | 4.32 |
| Water | 8000.0 mL | 90.93 |
| Total | 8797.5 | 100.00 |
| Aqueous Suspension Medium |  |  |
| Water | 7000.0 mL |  |
| Acacia | 1000.0 gm |  |
| Temperature | 45.0° C. |  |
| Suspension stirring speed | 300 rpm |  |
| Time | 24 hrs |  |

The resultant microbeads were 5.82% crosslinked.

TABLE 22

|  | Amount | Weight % in HIPE |
|---|---|---|
| HIPE |  |  |
| Lauroyl peroxide | 10.0 gm | 0.11 |
| 1% Ethyl cellulose in dichloromethane | 400.0 mL | 4.39 |
| Span ™ 80 | 120.0 gm | 1.32 |
| DVB | 270.0 gm | 2.96 |
| Styrene | 320.0 gm | 3.51 |
| Water | 8000.0 mL | 87.72 |
| Total | 9120.0 | 100.00 |
| Aqueous Suspension Medium |  |  |
| Water | 7000.0 mL |  |
| Acacia | 1100.0 gm |  |
| Temperature | 45.0° C. |  |
| Suspension stirring speed | 154 rpm |  |
| Time | 24 hrs |  |

The resultant microbeads were 25.17% crosslinked.

TABLE 23

|  | Amount | Weight % in HIPE |
|---|---|---|
| HIPE |  |  |
| Lauroyl peroxide | 10.5 gm | 0.12 |
| 1% Ethyl cellulose in trichloroethane | 200.0 mL | 2.31 |
| Span ™ 80 | 160.0 gm | 1.85 |
| DVB (55%) | 150.0 gm | 1.73 |
| Styrene | 145.0 gm | 1.67 |
| Water | 8000.0 mL | 92.32 |
| Total | 8665.5 | 100.00 |
| Aqueous Suspension Medium |  |  |
| Water | 7000.0 mL |  |
| Acacia | 1000.0 gm |  |
| Temperature | 45.0° C. |  |
| Suspension stirring speed | 300 rpm |  |
| Time | 24 hrs |  |

The resultant microbeads were 27.97% crosslinked.

TABLE 24

|  | Amount | Weight % in HIPE |
|---|---|---|
| HIPE |  |  |
| Lauroyl peroxide | 10.0 gm | 0.12 |
| 1% Ethyl cellulose in trichloroethane | 300.0 mL | 3.46 |
| Span ™ 80 | 160.0 gm | 1.85 |
| DVB (%) | 94.0 gm | 1.08 |
| Styrene | 100.0 gm | 1.15 |
| Water | 8000.0 mL | 92.34 |
| Total | 8664.0 | 100.00 |
| Aqueous Suspension Medium |  |  |
| Water | 8000.0 mL |  |
| Acacia | 1000.0 gm |  |
| Temperature | 45.0° C. |  |
| Suspension stirring speed | 314 rpm |  |
| Time | 24 hrs |  |

The resultant microbeads were 26.65% crosslinked.

EXAMPLE 6

Absorption Capacity of Hydrophilic Microbeads

The capacity of hydrophilic microbeads produced as described in Example 3 to absorb a 0.9% (weight/volume) saline solution was tested as follows. Microbeads were carefully weighed, and 0.200 gm (±0.005 gm) samples were placed in "teabags" designed for such tests and sealed. The teabags were 60 mm×60 mm and made from a grade 1234 heat-sealable material obtainable from C. H. Dexter, Division of Dexter Corp. (Windsor Locks, Conn.). The teabags were heat sealed on two of three sides, and the remaining open side was sealed after adding microbeads.

The sealed teabags were then immersed in the saline solution. Immersion was carried out by holding the teabags horizontally and ensuring that the microbeads were evenly distributed throughout the teabags, laying the teabags on the surface of the saline solution, and submerging the teabags after 1 min. After 30 mins of immersion, the teabags were hung for 10 mins to drain off excess saline and then weighed.

Saline absorption was calculated according to the following formula:

$$\text{Absorption} = \frac{(Wt_W - Wb_W) - Wp_D}{Wp_D}$$

where: $wt_W$ is the weight (in grams) of the wet microbead-containing tea bag, $Wb_W$ is the weight (in grams) of a wet empty tea bag, and $Wp_D$ is the weight (in grams) of the dry microbead sample. The results are shown in Table 25 (the components used to produce each microbead sample are listed in the tables indicated under the heading "Microbeads").

TABLE 25

| Microbeads | Crosslinking | Saline Absorption |
|---|---|---|
| Polyacrylamide/N,N'-methylene-bis-acrylamide (Table 11) | 4.99% | 95.56 gm* |
| Polyacrylic acid/N,N'-methylene-bis-acrylamide (Table 12) | 6.54% | 57.27 gm |
| Polyacrylic acid/N,N'-methylene-bis-acrylamide (Table 9) | 6.54% | 50.29 gm |

*gm water/gm dry polymer

EXAMPLE 7

Crosslinking and Retention Capacity of Hydrophilic Microbeads

The relationship between the degree of crosslinking and the capacity of hydrophilic microbeads to retain liquid was studied as follows. A series of hydrophilic microbeads having different degrees of crosslinking was tested for the capacity to retain a 0.9% (weight/volume) saline solution. These microbeads were produced as described in Example 3. This test was also performed using sulfonated polystyrene/divinylbenzene (DVB) microbeads produced as described in Example 5.

Microbeads were carefully weighed, and 0.200 gm (±0.005 gm) samples were placed in teabags, sealed, and immersed in the saline solution for 30 mins, as described in Example 6. The saturated teabags were then centrifuged in a IEC centrifuge (International Equipment Corp., Needham Heights, Mass.) at 3000 rpm (500 g) for 3 mins. The teabags were then carefully weighed. Saline absorption was calculated according to the following formula:

$$\text{Absorption} = \frac{(Wt_C - Wb_C) - Wp_D}{Wp_D}$$

where: $Wt_C$ is the weight (in grams) of the microbead-containing tea bag after centrifugation, $Wb_C$ is the weight (in grams) of an empty tea bag after centrifugation, and $Wp_D$ is the weight (in grams) of the dry microbead sample. The results are shown in Table 26 (the components used to produce each microbead sample are listed in the tables indicated under the heading "Microbeads").

TABLE 26

| Microbeads | Crosslinking | Saline Retention |
|---|---|---|
| Polyacrylic acid/N,N'-methylene-bis-acrylamide (Table 11) | 4.99% | 30.06 gm* |
| Polyacrylic acid/N,N'-methylene-bis-acrylamide (Table 12) | 6.54% | 16.85 gm |
| Polyacrylic acid/N,N'-methylene-bis-acrylamide (Table 9) | 6.54% | 15.26 gm |
| Polyacrylic acid/N,N'-methylene-bis-acrylamide (Table 9) | 6.54% | 13.89 gm |
| Polystyrene/DVB (Table 22) | 9.09% | 10.39 gm |
| Polystyrene/DVB (Table 23) | 25.93% | 2.67 gm |
| Polystyrene/DVB (Table 24) | 34.95% | 4.39 gm |

*gm saline/gm dry polymer

For the hydrophilic microbeads tested, saline absorption capacity is significantly influenced by, and inversely related to, degree of crosslinking. In contrast, for the sulfonated polystyrene/DVB microbeads, saline absorption capacity is less sensitive to changes in degree of crosslinking. Moreover, the saline absorption capacity of the sulfonated polystyrene/DVB microbeads is directly related to degree of crosslinking, at least up to 50% crosslinking.

EXAMPLE 8

Rate of Saline Absorption of Hydrophilic Microbeads

The capacity of hydrophilic microbeads to absorb a 0.9% (weight/volume) saline solution was measured at different time points after immersion.

Microbeads prepared as described in Example 3, Table 11 (4.99% crosslinked) were carefully weighed, and 0.200 gm (±0.005 gm) samples were placed in teabags (described in Example 6) and sealed. The sealed teabags were then immersed in the saline solution for 5, 10, 20, 30, or 60 seconds. The saturated teabags were hung for 2 mins to drain off excess saline and then weighed. Saline absorption was calculated according to the formula set forth in Example 6. The results are shown in Table 27.

TABLE 27

| Time | Saline Absorption |
|---|---|
| 5 sec | 42.70 gm* |
| 10 sec | 74.5 gm |
| 20 sec | 83.27 gm |
| 30 sec | 77.42 gm |
| 60 sec | 79.18 gm |

*gm saline/gm dry polymer

Thus, the hydrophilic microbeads had an extremely rapid rate of saline absorption, reaching maximal saline absorption capacity within 20 seconds and half maximal saline absorption capacity within 5 seconds.

EXAMPLE 9

Absorption of Hydrophilic Microbeads Under Load

The absorption capacity of hydrophilic microbeads under a static load was evaluated as follows. A test device consisted of a plastic cylinder (57.5 mm in diameter) with a screen epoxied to the bottom of the cylinder, and a plastic piston that fit inside the cylinder. Microbeads prepared as described in Example 3, Table 11 were distributed onto the screen of the test device, and the piston was inserted into the plastic cylinder so that it rested on top of the microbead sample. Additional weights were added to the piston to achieve a total weight of 535 gm (i.e., 20 gm/cm²). After assembly, the test device was weighed.

A fluid delivery assembly consisted of a porous filter plate placed in a petri dish. A 0.9% (weight/volume) saline solution was added to a level approximately equal to the top of the filter plate. A filter paper was then placed on the filter plate and allowed to wet with the saline solution.

The test device containing the microbead sample was placed on top of the filter plate so that the screen contacted the filter paper. The microbead sample was allowed to absorb saline solution from the filter paper for 1 hour. The test device was then reweighed, and saline absorption under load was calculated according to the following formula:

$$\text{Absorption} = \frac{Wt_W - Wt_D}{Wp_D}$$

where: $Wt_W$ is the weight (in grams) of the microbead-containing test device after water uptake, $Wt_D$ is the weight (in grams) of the microbead-containing test device before water uptake, and $Wp_D$ is the weight (in grams) of the dry microbead sample. The saline absorption under load was 25.90 gm±2.65 (S.D.) per gram of dry polymer.

What is claimed is:

1. A process for producing a porous crosslinked hydrophilic polymeric material comprising
   (a) forming an emulsion including a hydrophilic monomer continuous phase and an oil discontinuous phase, said emulsion comprising:
      i) a hydrophilic monofunctional monomer;
      ii) a polyfunctional crosslinker;
      iii) an emulsifier having a hydrophobic cyclic head group and a hydrophilic tail;
      iv) a stabilizer that is a film-forming compound; and
      v) an organic solvent; and
   (b) polymerizing the emulsion.

2. The process of claim 1 wherein the oil discontinuous phase of the emulsion is between about 50% to about 99% of the emulsion.

3. The process of claim 2 wherein the oil discontinuous phase of the emulsion is between about 70% to about 99% of the emulsion.

4. The process of claim 1 wherein the monomer comprises a monomer selected from the group consisting of acrylamide, acrylic acid, and derivatives thereof.

5. The process of claim 1 wherein the monomer concentration in the emulsion is in the range of about 0.5 to about 30 weight percent.

6. The process of claim 1 wherein the crosslinker comprises an agent selected from the group consisting of N,N'-methylene-bis-acrylamide, divinyl sulfone, diethylene glycol divinyl ether, and ethylene glycol dimethacrylate.

7. The process of claim 1 wherein the crosslinker concentration in the emulsion is in the range of about 0.005 to about 30 weight percent.

8. The process of claim 1 wherein the emulsifier comprises an alkylaryl polyether alcohol preparation.

9. The process of claim 8 wherein the alkylaryl polyether alcohol preparation is characterized by an average of at least about 14 ethylene oxide units per ether side chain.

10. The process of claim 1 wherein the emulsifier concentration in the emulsion is in the range of about 1 to about 30 weight percent.

11. The process of claim 1 wherein the stabilizer comprises a natural or synthetic polymeric stabilizer.

12. The process of claim 11 wherein the polymeric stabilizer comprises a cellulose derivative.

13. The process of claim 12 wherein the cellulose derivative is selected from the group consisting of methyl cellulose and hydroxyethyl cellulose.

14. The process of claim 1 wherein the stabilizer concentration in the emulsion is in the range of about 0.001 to about 2 weight percent.

15. The process of claim 1 wherein the emulsion additionally comprises a hydrophilic polymerization initiator.

16. The process of claim 15 wherein the hydrophilic polymerization initiator comprises ammonium persulfate.

17. The process of claim 15 wherein the hydrophilic polymerization initiator concentration is in the range of about 0.01 to about 10 weight percent of total polymerizable monomer.

18. The process of claim 1 wherein, prior to said polymerizing step, the emulsion is added to an oil suspension medium to form a suspension of emulsion droplets, and said polymerizing step comprises polymerizing the emulsion droplets to form microbeads.

19. The process of claim 18 wherein the oil suspension medium comprises a suspending agent.

20. The process of claim 19 wherein the suspending agent comprises a polymeric suspending agent.

21. The process of claim 20 wherein the polymeric suspending agent comprises a cellulose derivative.

22. The process of claim 21 wherein the cellulose derivative is selected from the group consisting of methyl cellulose and ethyl cellulose.

23. The process of claim 18 wherein the suspending agent is present in the oil suspension medium at a concentration of about 0.01 to about 10 weight percent.

24. The process of claim 18 wherein the ratio of oil suspension medium to emulsion in the suspension is in the range of about 0.05 to about 10.

25. The process of claim 1 additionally comprising adding a hydrophilic solvent to the oil suspension medium after said polymerizing step.

26. The process of claim 25 wherein the hydrophilic solvent comprises methanol.

27. A process for producing a porous crosslinked hydrophilic polymeric material comprising
   (a) forming an emulsion including a hydrophilic monomer continuous phase and an oil discontinuous phase, said emulsion comprising:
      i) a monomer selected from the group consisting of acrylamide, acrylic acid, and derivatives thereof;
      ii) a crosslinker selected from the group consisting of N,N'-methylene-bis-acrylamide and divinyl sulfone;
      iii) an alkylaryl polyether alcohol preparation having an average of at least about 14 ethylene oxide units per ether side chain;
      iv) ammonium persulfate;
      v) a solution of methyl cellulose in water; and
      vi) toluene;
      wherein the oil discontinuous phase is about 70% to about 99% of the emulsion, and substantially all of the polymerization initiator is present in the aqueous continuous phase of the emulsion; and
   (b) polymerizing the emulsion.

28. A process for producing porous crosslinked hydrophilic polymeric microbeads comprising
  (a) forming an emulsion including a hydrophilic monomer continuous phase and an oil discontinuous phase, said emulsion comprising:
    i) a monomer selected from the group consisting of acrylamide, acrylic acid, and derivatives thereof;
    ii) a crosslinker selected from the group consisting of N,N'-methylene-bis-acrylamide and divinyl sulfone;
    iii) an alkylaryl polyether alcohol preparation having an average of at least about 14 ethylene oxide units per ether side chain;
    iv) ammonium persulfate;
    v) a solution of methyl cellulose in water; and
    vi) toluene;
    wherein the oil discontinuous phase is about 70% to about 99% of the emulsion, and substantially all of the polymerization initiator is present in the aqueous continuous phase of the emulsion;
  (b) adding the emulsion to an oil suspension medium to form a suspension of emulsion droplets, wherein the suspension medium comprises ethyl cellulose; and
  (c) polymerizing the emulsion droplets to form microbeads.

* * * * *